United States Patent
Kim et al.

(10) Patent No.: US 10,214,489 B2
(45) Date of Patent: *Feb. 26, 2019

(54) SPIRO ORGANIC COMPOUNDS

(71) Applicant: NANJING TOPTO MATERIALS CO., LTD., Nanjing (CN)

(72) Inventors: Jin Woo Kim, Nanjing (CN); Chao Qian, Nanjing (CN); Jun Xu, Nanjing (CN); Dening Wang, Nanjing (CN)

(73) Assignee: NANJING TOPTO MATERIALS CO., LTD., Nanjing (CN)

( * ) Notice: Subject to any disclaimer, the term of this patent is extended or adjusted under 35 U.S.C. 154(b) by 165 days.

This patent is subject to a terminal disclaimer.

(21) Appl. No.: 15/339,068

(22) Filed: Oct. 31, 2016

(65) Prior Publication Data

US 2017/0125684 A1 May 4, 2017

(30) Foreign Application Priority Data

Oct. 30, 2015 (CN) .......................... 2015 1 0732925

(51) Int. Cl.
| | |
|---|---|
| *C07D 213/74* | (2006.01) |
| *H01L 51/00* | (2006.01) |
| *H01L 51/50* | (2006.01) |
| *C07C 25/22* | (2006.01) |
| *C07F 5/02* | (2006.01) |
| *C07D 307/91* | (2006.01) |

(52) U.S. Cl.
CPC ............ *C07D 213/74* (2013.01); *C07C 25/22* (2013.01); *C07D 307/91* (2013.01); *C07F 5/025* (2013.01); *H01L 51/006* (2013.01); *H01L 51/0052* (2013.01); *H01L 51/0058* (2013.01); *H01L 51/0061* (2013.01); *H01L 51/0067* (2013.01); *H01L 51/0072* (2013.01); *H01L 51/0073* (2013.01); *H01L 51/5012* (2013.01); *H01L 51/5056* (2013.01); *H01L 51/5072* (2013.01)

(58) Field of Classification Search
CPC .. C07D 307/91; C07D 209/86; C07D 209/88; C07D 213/74; C07D 307/09; H01L 51/0052; H01L 51/0056; H01L 51/0058; H01L 51/006; H01L 51/0061; H01L 51/0072; H01L 51/0073; H01L 51/5012; H01L 51/5056; H01L 51/5072; C07C 211/54; C07C 211/61; C07C 13/72; C07C 2603/95; C07C 2603/96; C07C 2603/97; C07C 2603/93; C07C 25/22; C07C 211/06; C09K 11/00; C09K 2211/1011; C09K 2211/1416
See application file for complete search history.

(56) References Cited

U.S. PATENT DOCUMENTS 5,840,217 A 11/1998 Lupo et al.

*Primary Examiner* — Jennifer A Chriss
*Assistant Examiner* — Elizabeth M. Dahlburg
(74) *Attorney, Agent, or Firm* — Buchanan Ingersoll & Rooney PC

(57) ABSTRACT

The present invention provides a spiro compound of General Formula 1, and use thereof in the fields of electronic materials, fine chemistry, and medical science. Further, the present invention also provides an organic electroluminescence device fabricated by using the spiro compound of General Formula 1. When used in an organic electroluminescence device, the compound of General Formula 1 provided in the present invention is capable of reducing the drive voltage, and increasing the luminous efficiency, brightness, thermal stability, color purity, and service life of the device.

[General Formula 1]

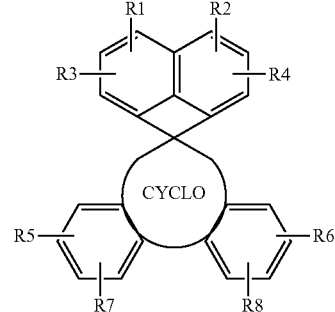

7 Claims, No Drawings

SPIRO ORGANIC COMPOUNDS

FIELD OF THE INVENTION

The present invention relates to a novel organic compound, and particularly to a spiro organic compound useful in the fields of electronic materials, fine chemistry, and medical science.

DESCRIPTION OF RELATED ART

In recent years, spiro organic compounds are mostly used in the field of electronic materials. However, besides the use in the field of electronic materials, the spiro organic compounds can also be widely used in the fields of fine chemistry, medical science, and others. The prior art is described below centering at the use in the field of electronic materials, particularly in the field of organic electroluminescence devices.

Organic electroluminescence devices utilizing organic electroluminescence generally have a structure including an anode, a cathode and an organic layer sandwiched therebetween. Here, the organic layer is provided for increasing the efficiency and stability of the organic electroluminescence devices, and generally has a multi-layer structure in which each layer is formed with a different substance. The multilayer structure includes, for example, a hole injection layer, a hole transport layer, an emission layer, an electron transport layer, an electron injection layer, etc. In the structure of such organic electroluminescence devices, when a voltage is applied between the two electrodes, holes are injected from the anode into the organic layer, and electrons are injected from the cathode to the organic layer. Excitons are formed when the injected holes and electrons encounter, and light is emitted when the excitons fall back to the ground state. The organic electroluminescence devices are distinguished by the characteristics of self-luminosity, high brightness, high efficiency, low drive voltage, wide viewing angle, high contrast, and high-speed response.

In the organic electroluminescence devices, the materials used as the organic layer may be classified, according to their functions, into emission materials and charge transport materials, for example, hole injection material, hole transport material, electron transport material, electron injection material and so on. The emission materials may be classified, according to the color of the light emitted, into blue, green and red light emitting materials, as well as yellow and orange light emitting materials for presenting a relatively better natural color. Moreover, to increase the color purity and increase the luminous efficiency through energy transfer, as an emission material, a host/dopant may be used. The underlying principle is that compared with the host substantially forming the emission layer, when a small amount of a dopant with a small energy gap and an excellent luminous efficiency is blended into the emission layer, the excitons generated in the host are transferred to the dopant, such that light is emitted with a high efficiency. In this case, the wavelength of the host is shifted with reference to the wavelength of the dopant, whereby light having desired wavelength can be obtained depending on the species of the dopants used.

To fully exert the excellent characteristics of the organic electroluminescence devices, substances forming the organic layer in the device, for example, the hole injection substance, the hole transport substance, the emission substance, the electron transport substance, and the electron injection substance should be preferentially formed of stable and efficient materials.

For example, when the thermal stability of the material decreases, the material is crystallized at a high temperature or at the drive temperature, which is a cause of shortened service life of the device. Typical examples include a dinaphthylanthracene compound, which has an up-to-down and left-to-right symmetrical molecular structure and thus is prone to crystallization with the rising of the temperature of the device. Recently, a spiro structure is introduced to prevent such crystallization, and improve the stability of the thin film. For example, U.S. Pat. No. 5,840,217 discloses spirobifluorene derivatives including spiro-benzene, spiro-DPVBi, and other monomeric molecules. However, although the generally known spiro compounds have excellent thermal stability, they suffer from the drawbacks of high drive voltage or inability to emit light with a high efficiency. Thus the use is mainly restricted to the blue light emitting materials.

Therefore, an organic electroluminescence device is proposed that can realize emitting of any colors of light by changing the structure of the organic substance used in the organic electroluminescence device, or that utilizes various methods through which high efficiency is achieved with the aid of a host-dopant system. However, a satisfactory brightness, characteristics, service life, and persistence cannot be attained at present.

PRIOR ART LITERATURES

Patent Document

U.S. Pat. No. 5,840,217

SUMMARY OF THE INVENTION

Technical Problem

The present invention aims at providing a novel organic compound useful in the field of electronic materials, fine chemistry, and medical science.

Further, an objective of the present invention is to provide a novel organic compound, which can be used in organic electroluminescence devices as a hole injection layer substance, a hole transport layer substance, an electron blocking layer substance, an emission layer substance, a hole blocking layer substance, an electron transport layer substance, and an electron injection layer substance, and when used in the organic electroluminescence devices, can reduce the drive voltage, and increase the luminous efficiency, luminance, thermal stability, color purity and service life of the devices.

Furthermore, the present invention aims at an organic electroluminescence device using the organic compound.

Means to Solve the Problem

The present invention provides a novel organic compound represented by General Formula 1 below:

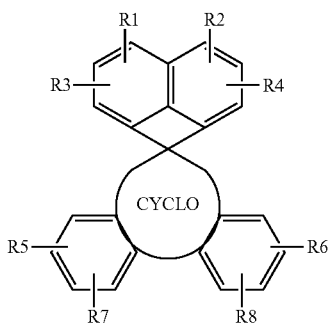

[General Formula 1]

where

CYCLO is a ring having 4 or 5 carbon atoms, where the CYCLO is a ring having 4 carbon atoms, two phenyl groups forming the CYCLO are taken together to form a naphthyl group; and R1, R2, R3, R4, R5, R6, R7 and R8 are each independently hydrogen, deuterium, F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, or a cycloalkyl having 3 to 40 carbon atoms, or an aromatic hydrocarbyl having 6 to 60 carbon atoms, which is unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, a cycloalkyl having 3 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl;

or a heteroaromatic hydrocarbyl having 5 to 60 carbon atoms and one or more heteroatoms selected from the group consisting of S, O, N, and Si, which is unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, a cycloalkyl having 3 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl, or an amino group substituted with one or more selected from the group consisting of phenyl, biphenyl, naphthyl, anthryl, anthryl substituted with phenyl, phenanthryl, pyrenyl, 9,9-dimethylfluorenyl, carbazolyl, quinolinyl, dibenzofuranyl, pyrrolyl, triazolyl, pyridinyl, pyrazinyl, and pyrimidinyl, where the phenyl, biphenyl, naphthyl, anthryl, and the phenyl substituent attached to the anthryl group are unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, and a cycloalkyl having 3 to 40 carbon atoms.

The organic compound is useful in the areas of electronic materials, fine chemistry, and medical science.

The present invention provides an organic electroluminescence device, which has one or more organic thin film layers, including at least an emission layer, sandwiched between a cathode and an anode. The organic electroluminescence device is characterized in that at least one of the organic thin film layers contains one or two or more of the organic compounds above.

Beneficial Effect of the Invention

The organic compound according to the present invention is useful in the fields of electronic materials, fine chemistry, and medical science.

Moreover, the organic compound can be used in organic electroluminescence devices as a hole injection layer substance, a hole transport layer substance, an electron blocking layer substance, an emission layer substance, a hole blocking layer substance, an electron transport layer substance, and an electron injection layer substance, and when used in the organic electroluminescence devices, can reduce the drive voltage, and increase the luminous efficiency, brightness, thermal stability, color purity and service life of the devices.

Furthermore, the organic electroluminescence device fabricated by using the organic compound of the present invention has the advantages of high efficiency and long service life.

DETAILED DESCRIPTION

The present invention provides a novel organic compound represented by General Formula 1 below:

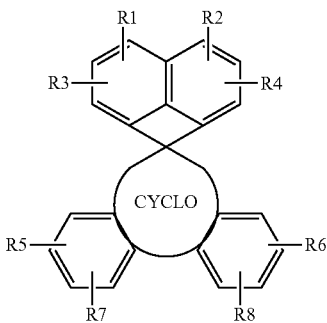

[General Formula 1]

where CYCLO is a ring having 4 or 5 carbon atoms, where the CYCLO is a ring having 4 carbon atoms, two phenyl groups forming the CYCLO are taken together to form a naphthyl group; and R1, R2, R3, R4, R5, R6, R7 and R8 are each independently hydrogen, deuterium, F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, or a cycloalkyl having 3 to 40 carbon atoms, or an aromatic hydrocarbyl having 6 to 60 carbon atoms, which is unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, a cycloalkyl having 3 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl, or a heteroaromatic hydrocarbyl having 5 to 60 carbon atoms and one or more elements selected from the group consisting of S, O, N, and Si, which is unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, a cycloalkyl having 3 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl, or an amino group substituted with one or more selected from the group consisting of phenyl, biphenyl, naphthyl, anthryl, anthryl substituted with phenyl, phenanthryl, pyrenyl, 9,9-dimethylfluorenyl, carbazolyl, quinolinyl, dibenzofuranyl, pyrrolyl, triazolyl, pyridinyl, pyrazinyl, and pyrimidinyl, where the phenyl, biphenyl, naphthyl, anthryl, and the phenyl substituent attached to the anthryl group are unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, and a cycloalkyl having 3 to 40 carbon atoms.

More preferably, General Formula (1) is represented by General Formula (2) or (3) below:

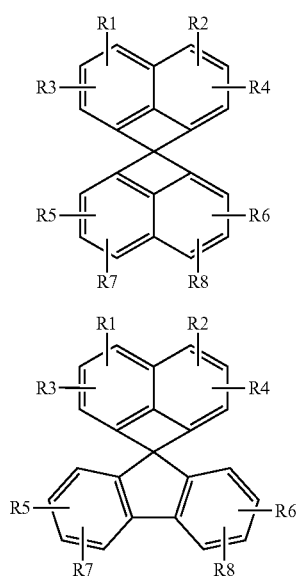

[General Formula 2]

[General Formula 3]

where R1, R2, R3, R4, R5, R6, R7, and R8 are each independently hydrogen, deuterium, F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, or a cycloalkyl having 3 to 40 carbon atoms, or an aromatic hydrocarbyl having 6 to 60 carbon atoms, which is unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, a cycloalkyl having 3 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl, or a heteroaromatic hydrocarbyl having 5 to 60 carbon atoms and one or more elements selected from the group consisting of S, O, N, and Si, which is unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, a cycloalkyl having 3 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl, or an amino group substituted with one or more selected from the group consisting of phenyl, biphenyl, naphthyl, anthryl, anthryl substituted with phenyl, pyrenyl, 9,9-dimethylfluorenyl, carbazolyl, quinolinyl, dibenzofuranyl, pyrrolyl, triazolyl, pyridinyl, pyrazinyl, and pyrimidinyl, where the phenyl, biphenyl, naphthyl, anthryl, and the phenyl substituent attached to the anthryl group are unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, and a cycloalkyl having 3 to 40 carbon atoms.

More preferably, in the formulas above,

R1, R2, R3, R4, R5, R6, R7 and R8 are each independently hydrogen, deuterium, F, Cl, Br, I, CN, $Si(CH_3)_3$, $B(OH)_2$, or a linear or branched alkyl having 1 to 40 carbon atoms, or phenyl, biphenyl, naphthyl, anthryl, phenanthryl, and pyrenyl unsubstituted or substituted with one or more selected from the group consisting of F, Cl, Br, I, $B(OH)_2$, a linear or branched alkyl having 1 to 40 carbon atoms, phenyl, biphenyl, naphthyl, anthryl, and phenyl or pyrrolyl, triazolyl, pyridinyl, pyrazinyl, pyrimidinyl, quinolinyl, 9,9-dimethylfluorenyl, carbazolyl or dibenzofuranyl unsubstituted or substituted with one or more selected from the group consisting of F, Cl, Br, I, $B(OH)_2$, a linear or branched alkyl having 1 to 10 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, and pyrimidinyl, or an amino group substituted with one or more selected from the group consisting of F, Cl, Br, I, $B(OH)_2$, a linear or branched alkyl having 1 to 10 carbon atoms, phenyl, biphenyl, naphthyl, anthryl, anthryl substituted with phenyl, phenanthryl, pyrenyl, 9,9-dimethylfluorenyl, carbazolyl, quinolinyl and dibenzofuranyl.

The compounds represented by General Formula (2) or (3) are any one of the compounds having general formulas below:

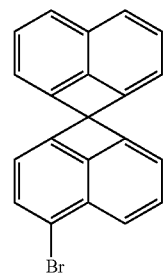

1

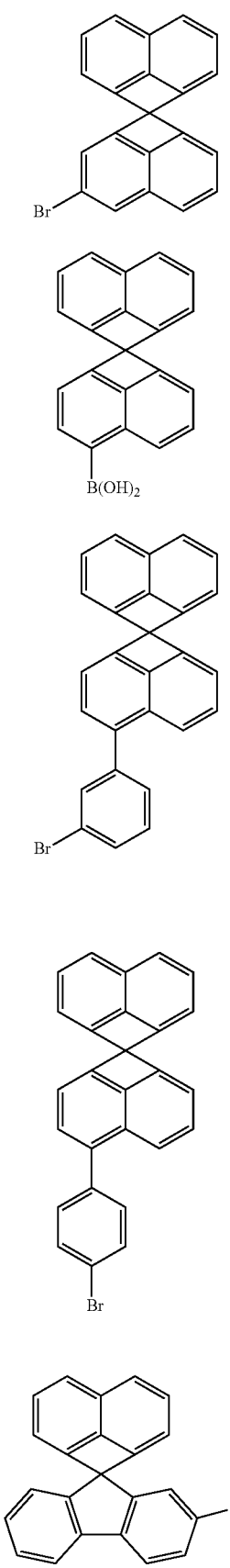
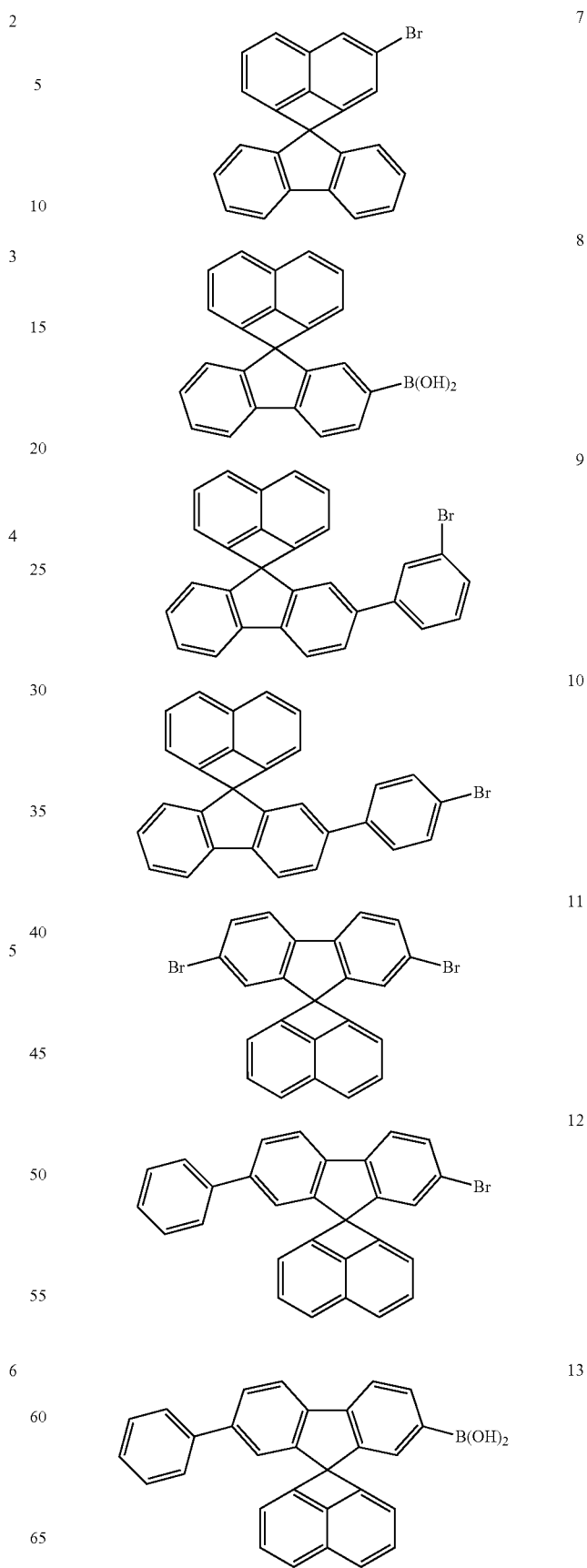

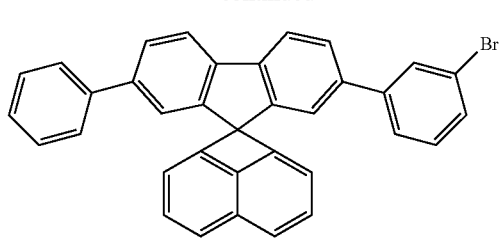
14
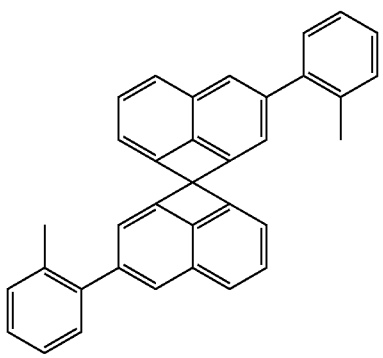
15
16
17
18
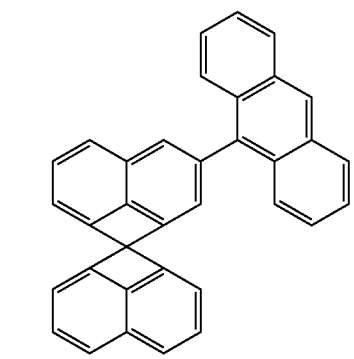
19
20
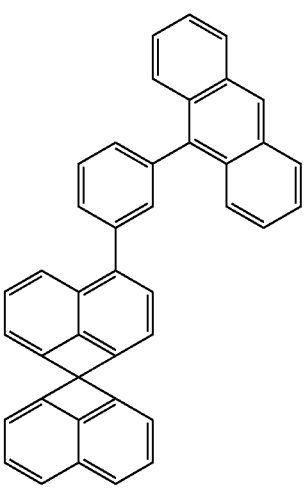
21
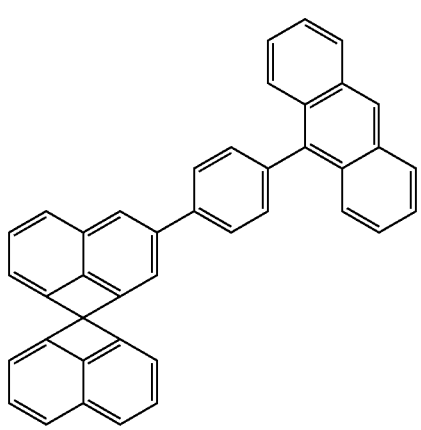
22

-continued
23
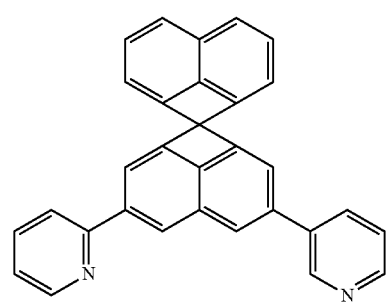
24
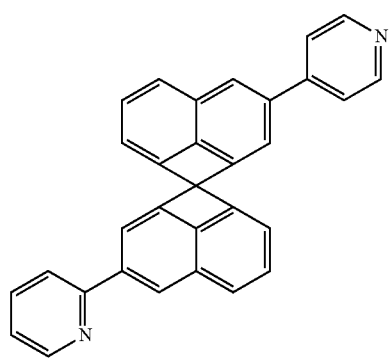
25
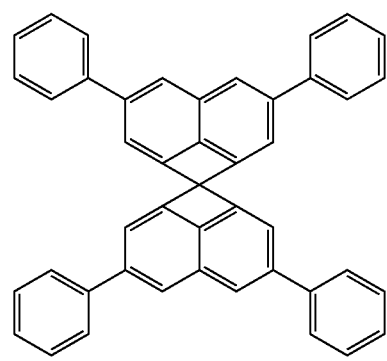
26
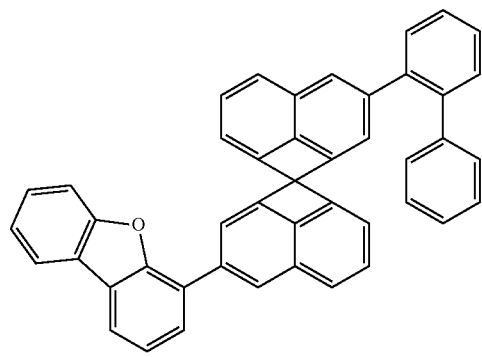
-continued
27
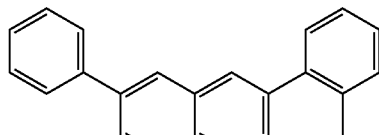
28
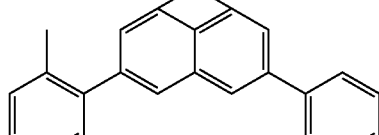
29
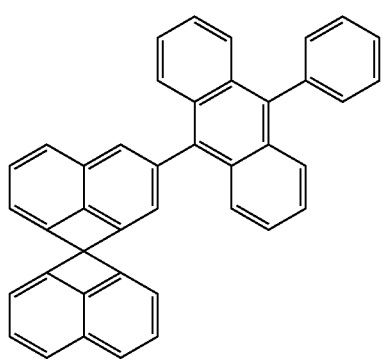
30
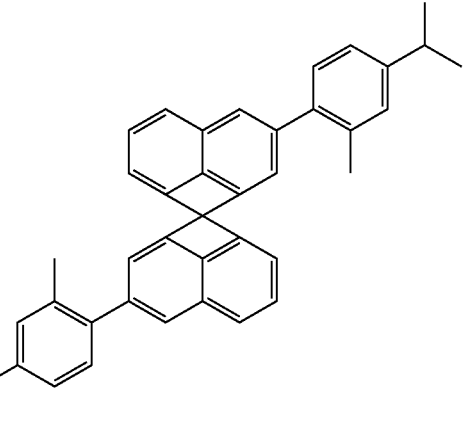

31
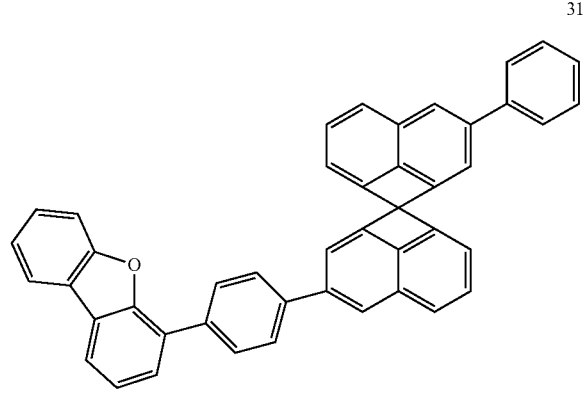
32
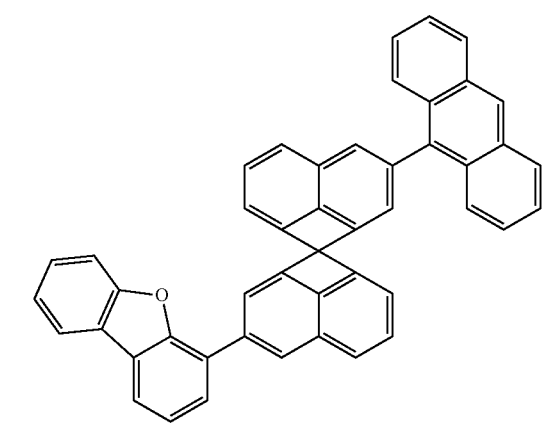
33
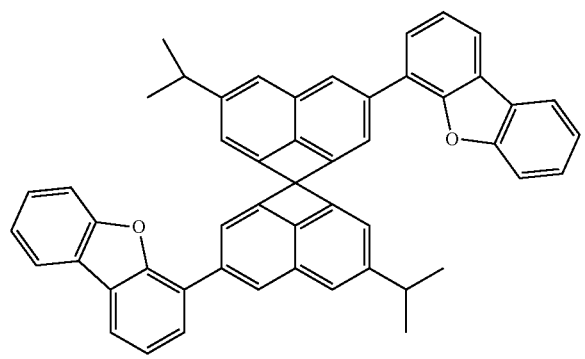
34
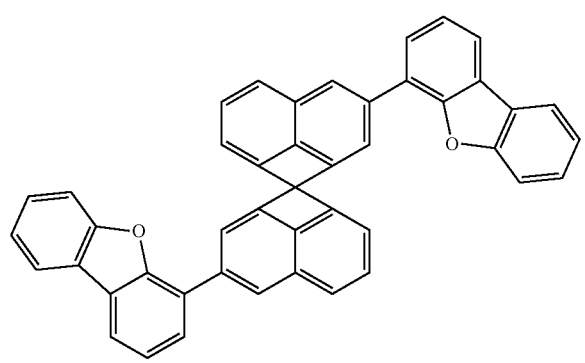
35
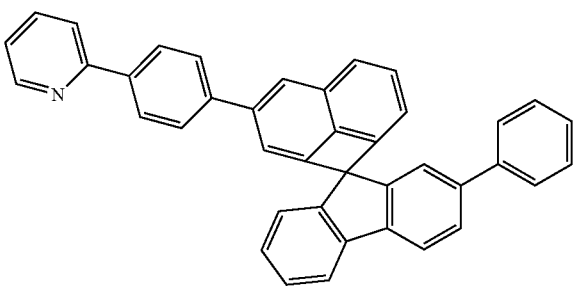
36
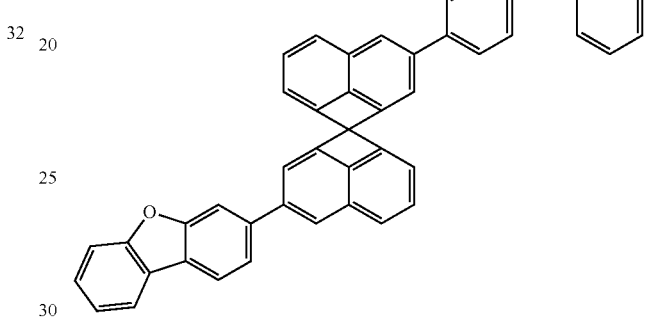
37
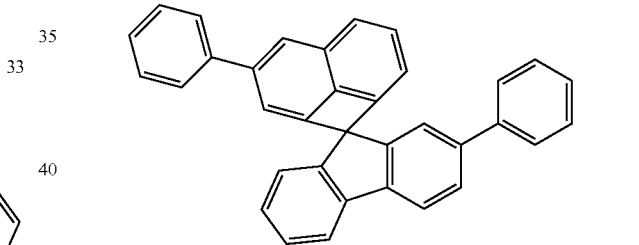
38
39
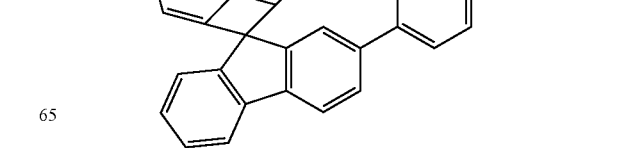

40
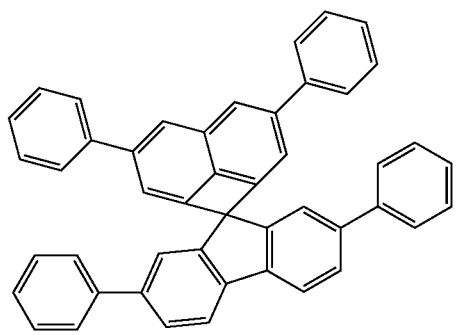
41
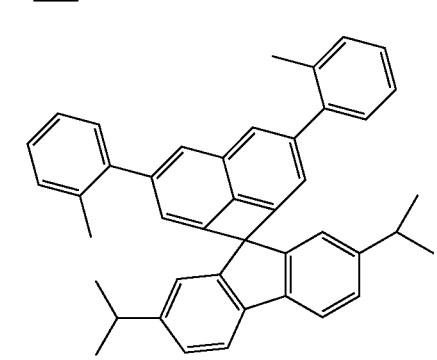
42
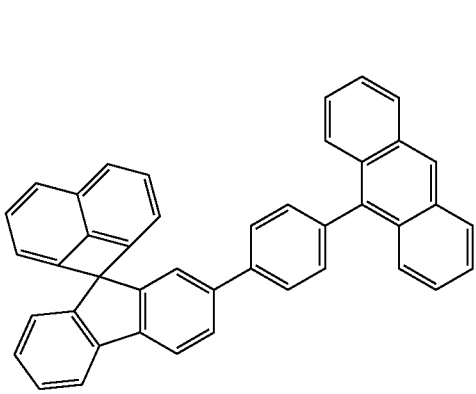
43
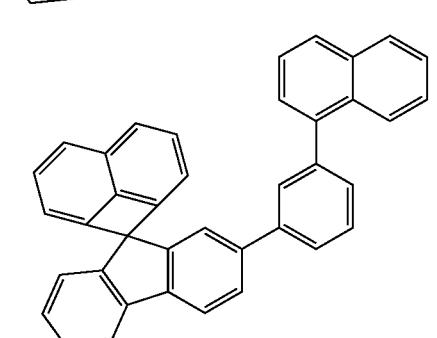
44
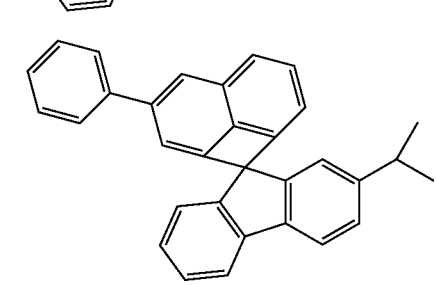
45
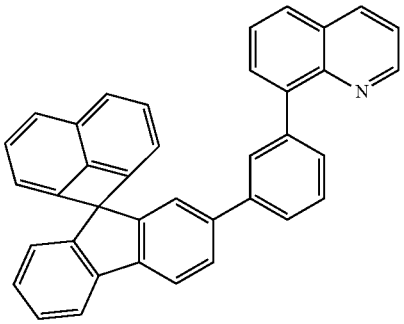
46
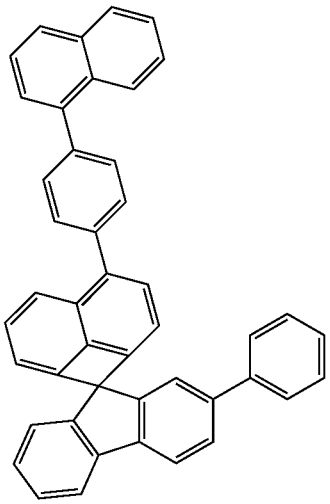
47
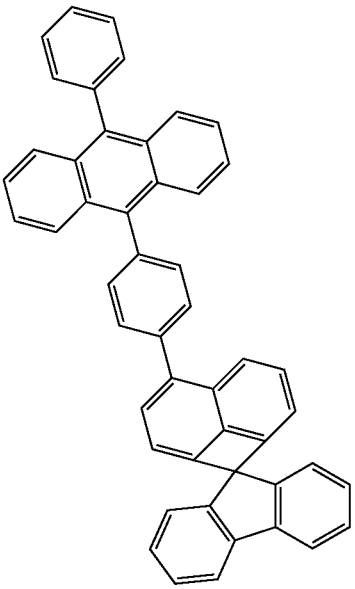

-continued

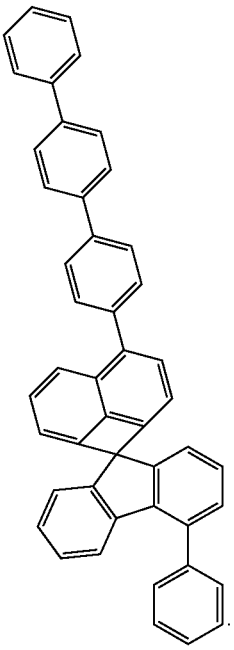

48

The organic compounds according to the present invention are useful in the field of electronic materials, fine chemistry, and medical science.

The organic compounds are not merely final compounds, and they may also be used as intermediates for synthesizing other compounds.

The organic compound can be used in organic electroluminescence devices as a hole injection layer substance, a hole transport layer substance, an electron blocking layer substance, an emission layer substance, a hole blocking layer substance, an electron transport layer substance, and an electron injection layer substance.

The present invention provides an organic electroluminescence device, which has one or more organic thin film layers, including at least an emission layer, sandwiched between a cathode and an anode. The organic electroluminescence device is characterized in that at least one of the organic thin film layers contains one or two or more of the organic compounds above.

The organic electroluminescence device has a structure comprising the anode, a hole injection layer, a hole transport layer, an electron blocking layer, the emission layer, an electron transport layer, an electron injection layer, and the cathode laminated in sequence.

Hereinafter, the organic electroluminescence device of the present invention is described by way of examples. However, the organic electroluminescence device of the present invention is not limited thereto.

The organic electroluminescence device of the present invention is fabricated by a process comprising the following steps.

Step 1: An anode material is laminated through a conventional process on a surface of a substrate to form an anode. The substrate used is a glass or transparent plastic substrate having good penetrability, surface smoothness, operability, and waterproof performance. Furthermore, the anode material may be transparent and highly conductive indium tin oxide (ITO), indium zinc oxide (IZO), tin dioxide ($SnO_2$), zinc oxide (ZnO), and so on.

Step 2: A hole injection layer (HIL) material is applied onto a surface of the anode through a conventional process by vacuum thermal deposition or by spin coating, to form a hole injection layer. The hole injection layer material may be CuPc, m-MTDATA, m-MTDAPB, and starburst amines TCTA, 2-TNATA, or IDE406 commercially available from Idemitsu Kosan Co., Ltd.

Step 3: A hole transport layer (HTL) material is applied onto a surface of the hole injection layer through a conventional process by vacuum thermal deposition or by spin coating, to form a hole transport layer. The hole transport layer material may be α-NPD, NPB, or TPD.

Step 4: An emission layer (EML) material is applied onto a surface of the hole transport layer through a conventional process by vacuum thermal deposition or by spin coating, to form an emission layer. The emission material may be a light-accumulating florescent material, a fluorescent brightener, a laser pigment, an organic scintillator, a fluorescent analytical reagent, and so on. Particularly, the emission material includes a carbazole compound, a phosphine oxide compound, a carbazole based phosphine oxide compound, FCNIrpic, $Alq_3$, anthracene, phenanthrene, pyrene, chrysene, perylene, coronene, rubrene, an polycyclic aromatic hydrocarbon compound such as quinacridone, a phenylene compound such as quaterphenyl, 1,4-bis(2-methylphenylvinyl)benzene, 1,4-bis(4-methyl-5-phenyl-2-azolyl)benzene, 1,4-bis(5-phenyl-2-azolyl) benzene, 2,5-bis(5-t-butyl-2-benzoxazoyl)thiophene, 1,4-biphenyl-1,3-butadiene, 1,6-biphenyl-1,3,5-hexatriene, a scintillator for liquid scintillation such as 1,1,4,4-tetraphenyl-1,3-butadiene, metal carriers for auxin derivatives, coumarin pigments, dicyanomethylene pigments, dicyanomethylene thiopyran pigments, polymethine pigments, hydroxybenzoanthracene pigments, xanthene pigments, quinolone pigments, perylene pigments, oxazine compounds, stilbene derivatives, spiro compounds, oxadiazole and so on.

Further, an electron blocking layer (EBL) may be added between the hole transport layer and the emission layer.

Step 5: An electron transport layer (ETL) material is applied onto a surface of the emission layer through a conventional process by vacuum thermal deposition or by spin coating, to form an electron transport layer. The electron transport layer material is not particularly limited, and preferably $Alq_3$.

Further, a hole blocking layer (HBL) may also be added between the emission layer and the electron transport layer, which, in combination with the use of a phosphorescent dopant in the emission layer, can prevent the triplet excitons or hole from diffusing into the electron transport layer.

A hole blocking layer (HBL) material is applied onto a surface of the emission layer through a conventional process by vacuum thermal deposition or by spin coating, to form a hole blocking layer. The hole blocking layer material is not particularly limited, and preferably Liq, bis(2-methyl-8-quinolinolato)-(1,1'-Biphenyl-4-olato)aluminum, BCP, and LiF etc.

Step 6: An electron injection layer (EIL) material is applied onto a surface of the electron transport layer through a conventional process by vacuum thermal deposition or by spin coating, to form an electron injection layer. The electron injection layer material may be LiF, Liq, $Li_2O$, BaO, NaCl, CsF, and so on.

Step 7: A cathode material is applied onto the electron injection layer through a conventional process by vacuum thermal deposition or by spin coating, to form a cathode. The cathode material may be Li, Al, Al—Li, Ca, Mg, Mg—In, Mg—Ag, and so on.

Furthermore, for the organic electroluminescence devices, a light penetrable transparent cathode can be fabricated when indium tin oxide (ITO) or indium zinc oxide (IZO) is used.

Further, according to the composition of the overlay above, a cathode protection layer (CPL) may be further formed on a surface of the cathode.

In the method for preparing the organic electroluminescence device, the device is fabricated in the order of anode/hole injection layer/hole transport layer/emission layer/electron transport layer/electron injection layer/cathode, and the device may also be fabricated in the order of cathode/electron injection layer/electron transport layer/emission layer/hole transport layer/hole injection layer/anode.

Hereinafter, methods for synthesizing the compounds of General Formula 1 are described by way of examples. However, the methods exemplified below are not intended to limit the methods for synthesizing the compounds of the present invention, and the compounds of the present invention may be prepared through the methods exemplified below and methods generally known in the art.

Synthesis of Intermediate 1

[Reaction equation 1]

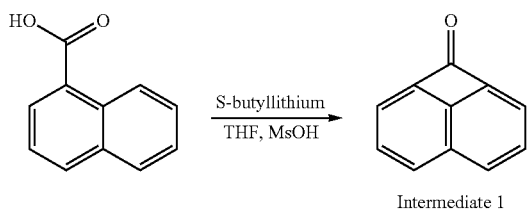

Under a nitrogen atmosphere, naphthalenecarboxylic acid (1.72 g, 10 mmol) was dissolved in tetrahydrofuran (10 mL), and mixed with 1.4 M s-butyllithium at −40° C. Then, the cold water bath was removed, and the reaction solution was stood for 30 min in a water bath at room temperature, stirred for 2 hrs, and cooled at −78° C. Tetrahydrofuran (10 mL) containing methanesulfonic acid (1.44 g, 15 mmol) was added dropwise. Then, the cold water bath was removed, and the resulting mixture was stood for 30 min in a water bath at room temperature, and refluxed at 60° C. for 2 hrs.

After the reaction was terminated, the reaction solution was washed with a saturated sodium chloride solution, and then a 2N aqueous HCl solution was added, stirred for 30 min, and then extracted with diethyl ether.

The organic layer was dried over anhydrous magnesium sulfate, suctioned, and concentrated. The resultant compound was purified by column chromatography eluting with Hex:EA=5:1, to obtain Intermediate 1 (0.79 g, 51%).

Intermediate 1 MS(FAB): 154(M$^+$)

Synthesis of Compound 1

[Reaction equation 2]

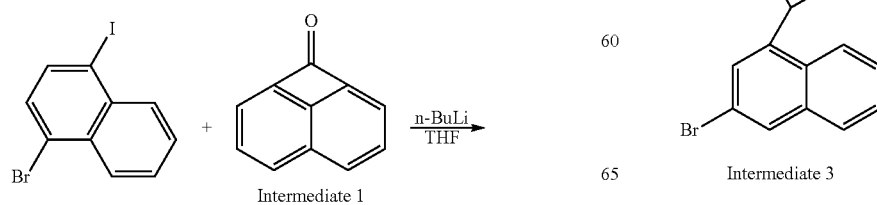

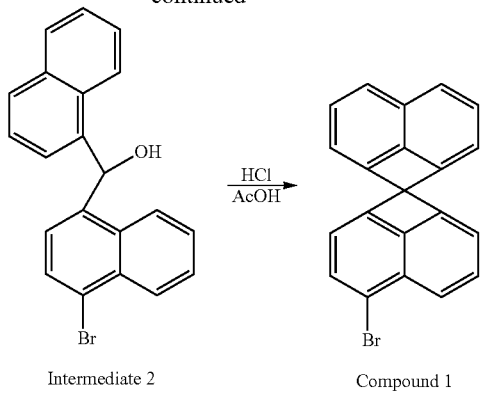

1-bromo-4-iodonaphthalene (3.33 g, 10 mmol) was dissolved in tetrahydrofuran (15 ml), and cooled to −78° C. n-butyllithium (2.5 M, 4 mL) was added dropwise, and stirred at −78° C. for 1 h. Intermediate 1 (1.54 g, 10 mmol) dissolved in tetrahydrofuran (30 mL) was slowly added dropwise, and warmed to normal temperature. After the reaction was terminated, MC and 2N HCl were added, and the organic layer was extracted.

The organic layer was dried over anhydrous magnesium sulfate, suctioned, and concentrated. The resultant compound was purified by column chromatography eluting with Hex:EA=5:1, to obtain Intermediate 2 (2.76 g, 76%).

Intermediate 2 was dissolved in acetic acid, and then concentrated hydrochloric acid was added dropwise, and refluxed for 1 hr. The reaction was terminated, and extracted with diethyl ether and water. The organic layer was washed with a saturated sodium bicarbonate solution in water, dried over magnesium sulfate, recrystallized, and purified by column chromatography eluting with Hex:EA=4:1, to obtain Compound 1 (2.85 g, 83%).

Intermediate 2 MS(FAB): 363(M$^+$)
Compound 1 MS(FAB): 343(M$^+$)

Synthesis of Compound 2

[Reaction equation 3]

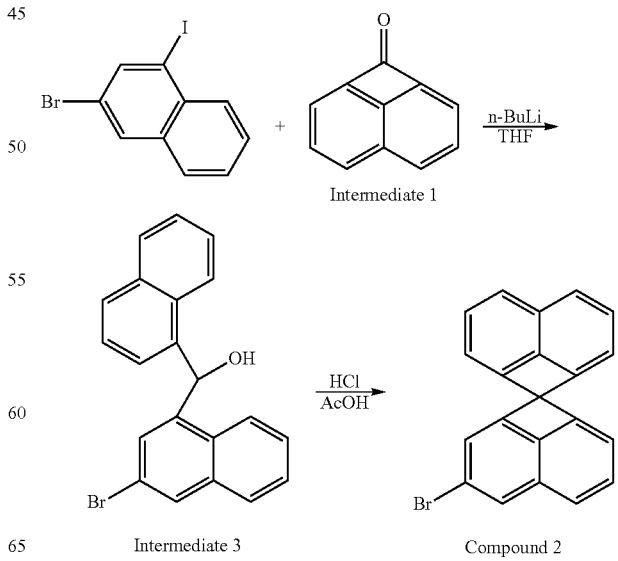

3-bromo-1-iodonaphthalene (3.33 g, 10 mmol) was dissolved in tetrahydrofuran (15 ml), and then cooled to −78° C. n-butyllithium (2.5 M, 4 mL) was added dropwise and stirred at −78° C. for 1 hr. Intermediate 1 (1.54 g, 10 mmol) dissolved in tetrahydrofuran (30 ml) was slowly added dropwise, and warmed to normal temperature. After the reaction was terminated, MC and 2N HCl were added, and the organic layer was extracted.

The organic layer was dried over anhydrous magnesium sulfate, suctioned, and concentrated. The resultant compound was purified by column chromatography eluting with Hex:EA=5:1, to obtain Intermediate 3 (2.72 g, 75%).

Intermediate 3 was dissolved in acetic acid, and then concentrated hydrochloric acid was added dropwise, and refluxed for 1 hr. The reaction was terminated, and extracted with diethyl ether and water. The organic layer was washed with a saturated sodium bicarbonate solution in water, dried over magnesium sulfate, recrystallized, and purified by column chromatography eluting with Hex:EA=4:1, to obtain Compound 2 (2.75 g, 80%).

Intermediate 3 MS(FAB): 363(M$^+$)
Compound 2 MS(FAB): 343(M$^+$)

Synthesis of Compound 3

[Reaction equation 4]

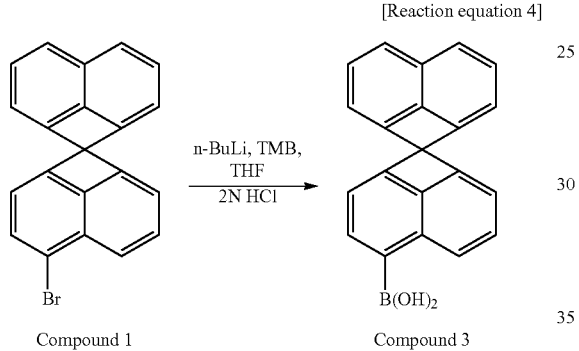

Compound 1    Compound 3

Under a nitrogen atmosphere, Compound 1 (3.43 g, 10 mmol) was dissolved in anhydrous tetrahydrofuran (40 mL), and cooled to −78° C. n-butyllithium (2.5 M, 4 mL) was slowly added dropwise, stirred at 0° C. for 1 hr, and then cooled to −78° C. again. Trimethyl borate (12.47 g, 12 mmol) was added dropwise, and stirred for 12 hrs at normal temperature. After the reaction was terminated, a 2N aqueous HCl solution was added, stirred for 30 min, and extracted with diethyl ether.

The organic layer was dried over anhydrous magnesium sulfate, suctioned, and concentrated. The resultant compound was purified by column chromatography eluting with Hex:EA=5:1, to obtain Compound 3 (2.43 g, 79%).

Compound 3 MS (FAB): 334(M$^+$)

Synthesis of Compound 4

[Reaction equation 5]

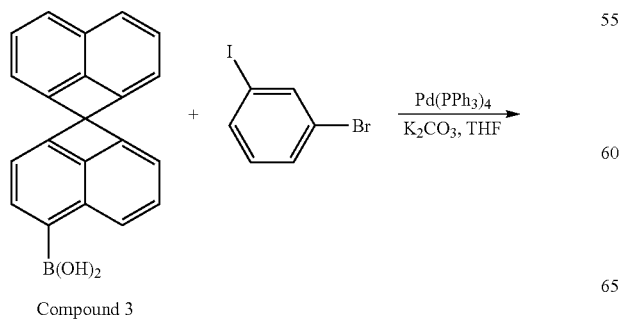

Compound 3

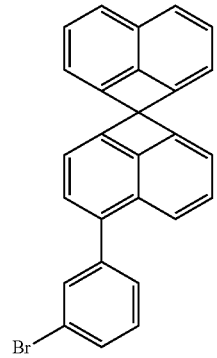

Compound 4

Under a nitrogen atmosphere, Compound 3 (3.08 g, 10 mmol) and m-bromoiodobenzene (2.83 g, 10 mmol) were dissolved in tetrahydrofuran (40 mL). Then Pd(PPh$_3$)$_4$ (0.58 g, 0.5 mmol) and K$_2$CO$_3$ (2 M, 15 mL, 30 mmol) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=5:1, to obtain Compound 4 (2.97 g, 71%).

$^1$H NMR (DMSO, 300 Hz): δ(ppm)=8.22-7.66 (m, 4H), 7.64-7.23 (m, 7H), 7.20-6.70 (d, 4H)

Compound 4 MS(FAB): 419(M$^+$)

Synthesis of Compound 5

[Reaction equation 6]

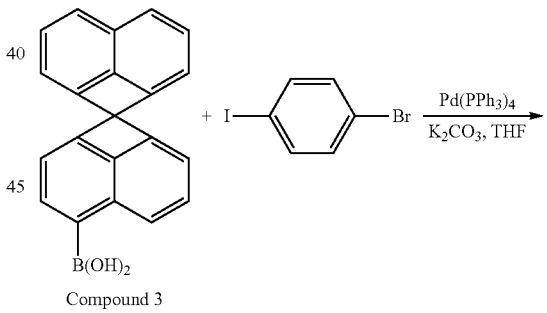

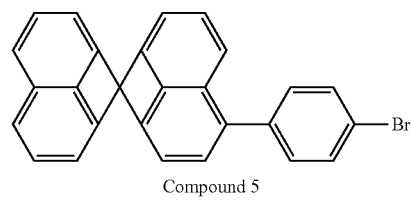

Compound 5

Under a nitrogen atmosphere, Compound 3 (3.08 g, 10 mmol) and 1-bromo-4-iodobenzene (2.83 g, 10 mmol) were mixed and dissolved in tetrahydrofuran (40 mL). Pd(PPh$_3$)$_4$ (0.58 g, 0.5 mmol) and K$_2$CO$_3$ (2 M, 15 ml, 30 mmol) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=4:1, to obtain Compound 5 (2.89 g, 69%).

$^1$H NMR (DMSO, 300 Hz): δ(ppm)=8.22-7.66 (m, 4H), 7.64-7.26 (m, 7H), 7.22-6.70 (d, 4H)

Compound 5 MS(FAB): 419(M$^+$)

column chromatography eluting with Hex:EA=5:1, to obtain Compound 6 (2.99 g, 81%).

Intermediate 4 MS(FAB): 387(M$^+$)

Compound 6 MS(FAB): 369(M$^+$)

Synthesis of Compound 6

[Reaction equation 7]

Synthesis of Compound 7

[Reaction equation 8]

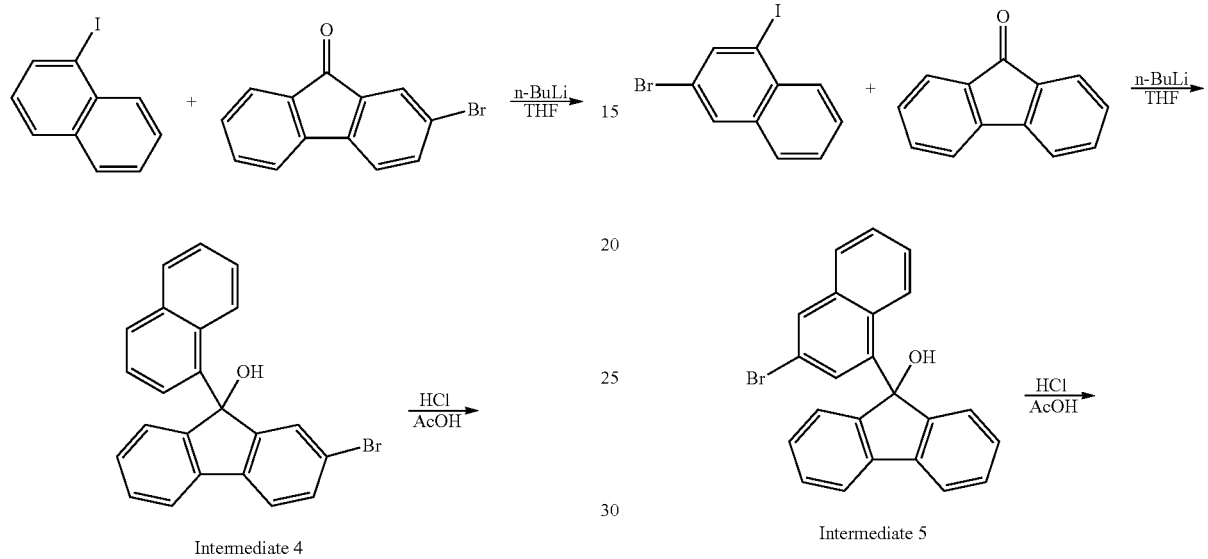

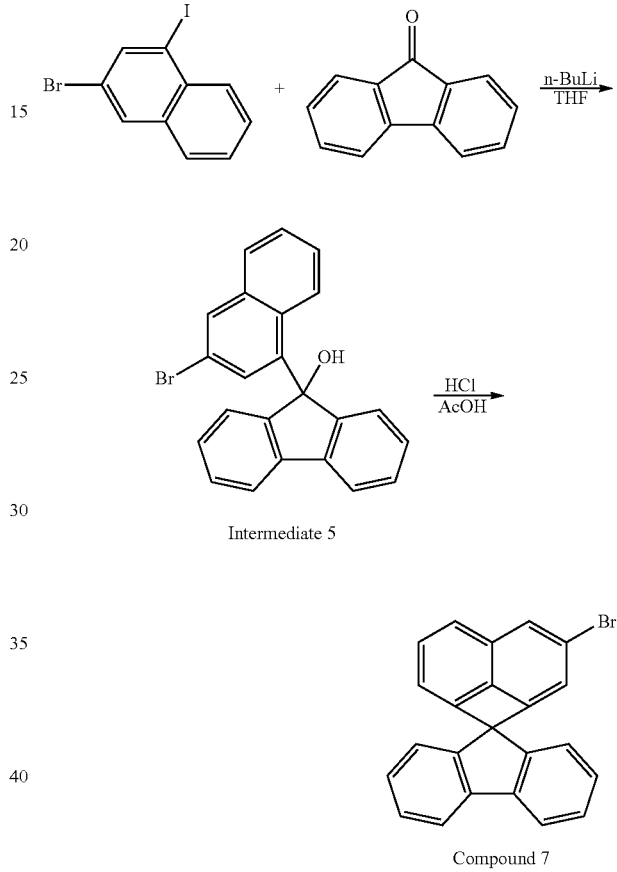

1-iodonaphthalene (2.54 g, 10 mmol) was dissolved in tetrahydrofuran (15 ml), and then cooled to −78° C. n-butyllithium (2.5 M, 4 mL) was added dropwise, and stirred at −78° C. for 1 hr. 2-bromo-9-fluorenone (2.59 g, 10 mmol) dissolved in tetrahydrofuran (30 ml) was slowly added dropwise, and warmed to normal temperature. After the reaction was terminated, MC and 2N HCl were added, and the organic layer was extracted.

The organic layer was dried over anhydrous magnesium sulfate, suctioned, and concentrated. The resultant compound was purified by column chromatography eluting with Hex:EA=5:1, to obtain Intermediate 4 (3.06 g, 79%).

Intermediate 4 was dissolved in acetic acid, and then concentrated hydrochloric acid was added dropwise, and refluxed for 1 hr. The reaction was terminated, and extracted with diethyl ether and water. The organic layer was washed with a saturated sodium bicarbonate solution in water, dried over magnesium sulfate, recrystallized, and purified by 3-bromo-1-iodonaphthalene (3.33 g, 10 mmol) was dissolved in tetrahydrofuran (15 ml), and then cooled to −78° C. n-butyllithium (2.5 M, 4 mL) was added dropwise, and stirred at −78° C. for 1 hr. 9-fluorenone (1.80 g, 10 mmol) dissolved in tetrahydrofuran (30 ml) was slowly added dropwise, and warmed to normal temperature. After the reaction was terminated, MC and 2N HCl were added, and the organic layer was extracted.

The organic layer was dried over anhydrous magnesium sulfate, suctioned, and concentrated. The resultant compound was purified by column chromatography eluting with Hex:EA=5:1, to obtain Intermediate 5 (2.48 g, 64%).

Intermediate 5 was dissolved in acetic acid, and then concentrated hydrochloric acid was added dropwise, and refluxed for 1 hr. The reaction was terminated, and extracted with diethyl ether and water. The organic layer was washed with a saturated sodium bicarbonate solution in water, dried over magnesium sulfate, recrystallized, and purified by column chromatography eluting with Hex:EA=4:1, to obtain Compound 7 (2.81 g, 76%).

Intermediate 5 MS(FAB): 387(M⁺)

Compound 7 MS(FAB): 369(M⁺)

Synthesis of Compound 8

[Reaction equation 9]

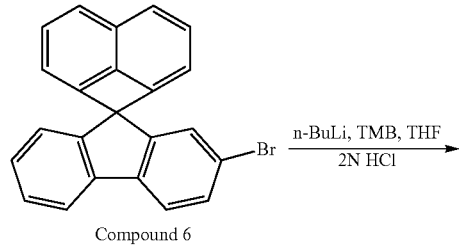

Compound 6

Compound 8

Under a nitrogen atmosphere, Compound 6 (3.69 g, 10 mmol) was dissolved in anhydrous tetrahydrofuran (40 mL), and cooled to −78° C. n-butyllithium (2.5 M, 4 mL) was slowly added dropwise, stirred at 0° C. for 1 hr, and then cooled to −78° C. again. Trimethyl borate (12.47 g, 12 mmol) was added dropwise, and stirred for 12 hrs at normal temperature. After the reaction was terminated, a 2N aqueous HCl solution was added, stirred for 30 min, and extracted with diethyl ether.

The organic layer was dried over anhydrous magnesium sulfate, suctioned, and concentrated. The resultant compound was purified by column chromatography eluting with Hex:EA=5:1, to obtain Compound 8 (2.47 g, 74%).

Compound 8 MS(FAB): 334(M⁺)

Synthesis of Compound 9

[Reaction equation 10]

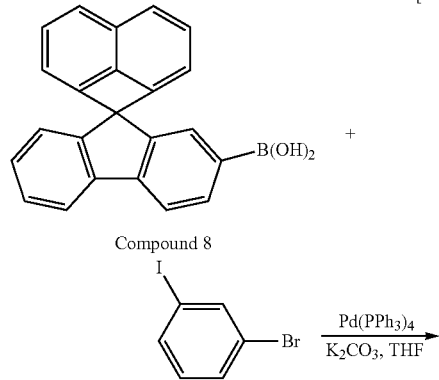

Compound 8

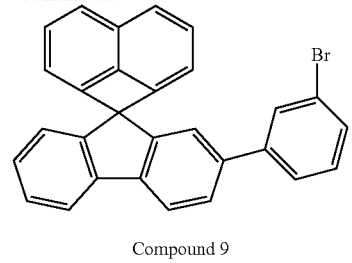

Compound 9

Under a nitrogen atmosphere, Compound 8 (3.34 g, 10 mmol) and 1-bromo-3-iodobenzene (2.83 g, 10 mmol) were dissolved in tetrahydrofuran (40 mL). Then Pd(PPh₃)₄ (0.58 g, 0.5 mmol) and K₂CO₃ (2 M, 15 mL, 30 mmol) were added and refluxed for 24 hrs.

After the reaction was terminated, the reactants were cooled to normal temperature, and MC (200 mL) and H₂O (200 mL) were added. The MC layer was extracted, dried over anhydrous magnesium sulfate, concentrated, and purified by column chromatography eluting with Hex:EA=5:1, to obtain Compound 9 (3.25 g, 73%).

¹H NMR (DMSO, 300 Hz): δ(ppm)=8.07-7.66 (m, 4H), 7.64-7.23 (m, 9H), 7.20-6.91 (m, 2H), 6.89-6.60 (d, 2H)

Compound 9 MS(FAB): 445(M⁺)

Synthesis of Compound 10

[Reaction equation 11]

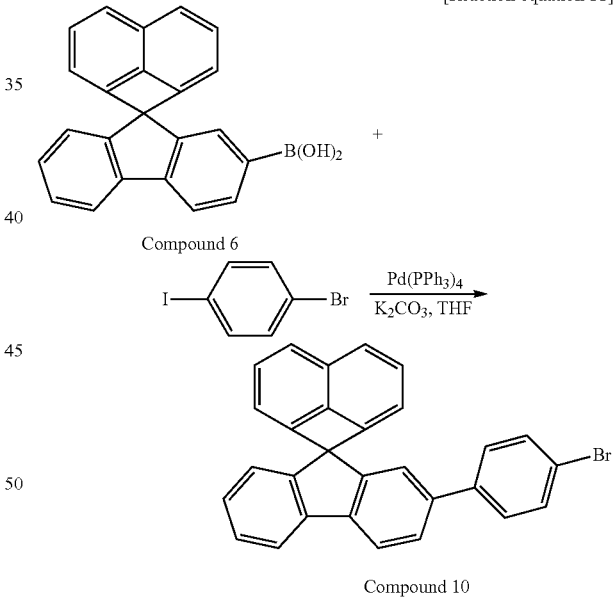

Compound 6

Compound 10

Under a nitrogen atmosphere, Compound 6 (3.34 g, 10 mmol) and 1-bromo-4-iodobenzene (2.83 g, 10 mmol) were mixed and dissolved in tetrahydrofuran (40 mL). Pd(PPh₃)₄ (0.58 g, 0.5 mmol) and K₂CO₃ (2 M, 15 ml, 30 mmol) were added and refluxed for 24 hrs.

After the reaction was terminated, the reactants were cooled to normal temperature, and MC (200 mL) and H₂O (200 mL) were added. The MC layer was extracted, dried over anhydrous magnesium sulfate, concentrated, and purified by column chromatography eluting with Hex:EA=4:1, to obtain Compound 10 (3.34 g, 75%).

¹H NMR (DMSO, 300 Hz): δ(ppm)=8.07-7.66 (m, 4H), 7.64-7.25 (m, 9H), 7.22-6.91 (m, 2H), 6.87-6.60 (d, 2H)

Compound 10 MS(FAB): 445(M⁺)

Synthesis of Compound 11

[Reaction equation 12]

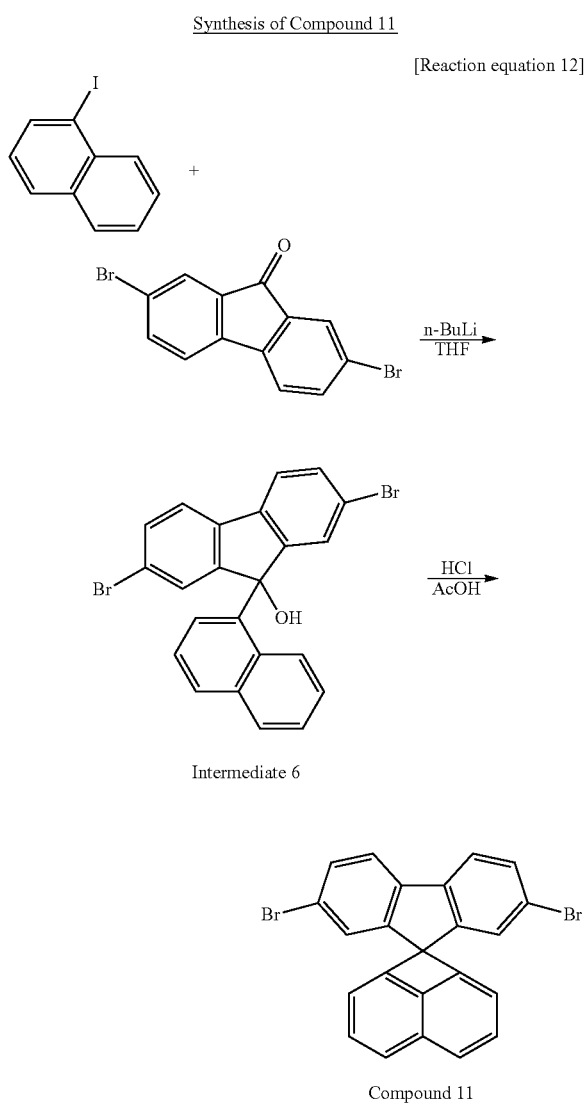

Intermediate 6

Compound 11

1-iodonaphthalene (2.54 g, 10 mmol) was dissolved in tetrahydrofuran (15 ml), and then cooled to −78° C. n-butyllithium (2.5 M, 4 mL) was added dropwise, and stirred at −78° C. for 1 hr. 2, 7-dibromo-9-fluorenone (3.38 g, 10 mmol) dissolved in tetrahydrofuran (30 ml) was slowly added dropwise, and warmed to normal temperature. After the reaction was terminated, MC and 2N HCl were added, and the organic layer was extracted.

The organic layer was dried over anhydrous magnesium sulfate, suctioned, and concentrated. The resultant compound was purified by column chromatography eluting with Hex:EA=3:1, to obtain Intermediate 6 (3.31 g, 71%).

Intermediate 6 was dissolved in acetic acid, and then concentrated hydrochloric acid was added dropwise, and refluxed for 1 hr. The reaction was terminated, and extracted with diethyl ether and water. The organic layer was washed with a saturated sodium bicarbonate solution in water, dried over magnesium sulfate, recrystallized, and purified by column chromatography eluting with Hex:EA=5:1, to obtain Compound 11 (3.45 g, 77%).

Intermediate 6 MS(FAB): 466(M⁺)

Compound 11 MS(FAB): 448(M⁺)

Synthesis of Compound 12

[Reaction equation 13]

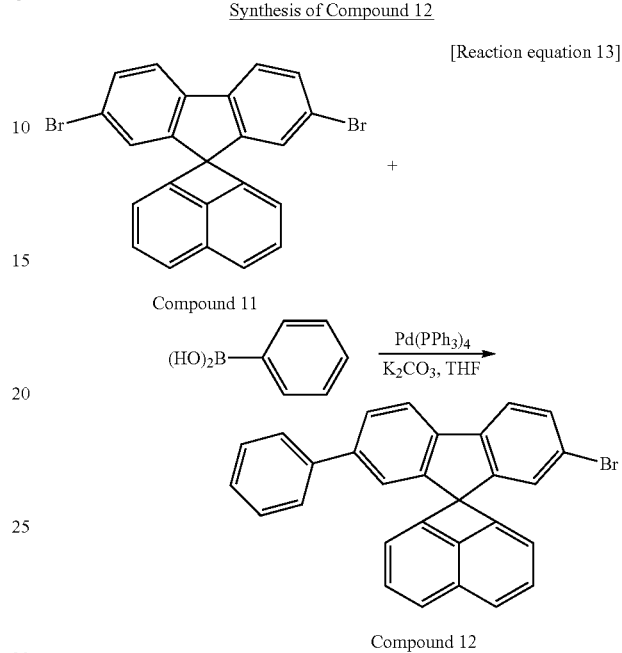

Compound 12

Under a nitrogen atmosphere, Compound 11 (4.48 g, 10 mmol) and phenylboronic acid (1.22 g, 10 mmol) were mixed and dissolved in tetrahydrofuran (40 mL). Pd(PPh₃)₄ (0.58 g, 0.5 mmol) and K₂CO₃ (2 M, 15 ml, 30 mmol) were added and refluxed for 24 hrs.

After the reaction was terminated, the reactants were cooled to normal temperature, and MC (200 mL) and H₂O (200 mL) were added. The MC layer was extracted, dried over anhydrous magnesium sulfate, concentrated, and purified by column chromatography eluting with Hex:EA=4:1, to obtain Compound 12 (3.16 g, 71%).

Compound 12 MS(FAB): 445(M⁺)

Synthesis of Compound 13

[Reaction equation 14]

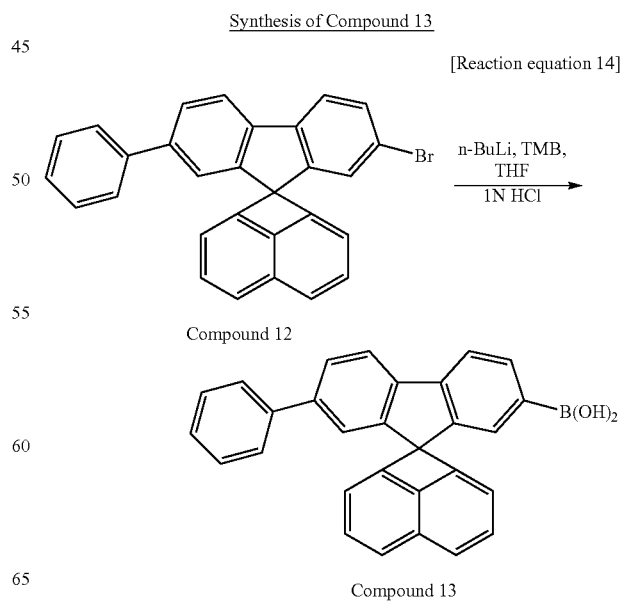

Compound 13

Under a nitrogen atmosphere, Compound 12 (3.69 g, 10 mmol) was dissolved in anhydrous tetrahydrofuran (40 mL), and cooled to −78° C. n-butyllithium (2.5 M, 4 mL) was slowly added dropwise, stirred at 0° C. for 1 hr, and then cooled to −78° C. again. Trimethyl borate (12.47 g, 12 mmol) was added dropwise, and stirred for 12 hrs at normal temperature. After the reaction was terminated, a 2N aqueous HCl solution was added, stirred for 30 min, and extracted with diethyl ether.

The organic layer was dried over anhydrous magnesium sulfate, suctioned, and concentrated. The resultant compound was purified by column chromatography eluting with Hex:EA=4:1, to obtain Compound 13 (3.04 g, 74%).

Compound 13 MS(FAB): 410(M$^+$)

Synthesis of Compound 14

[Reaction equation 15]

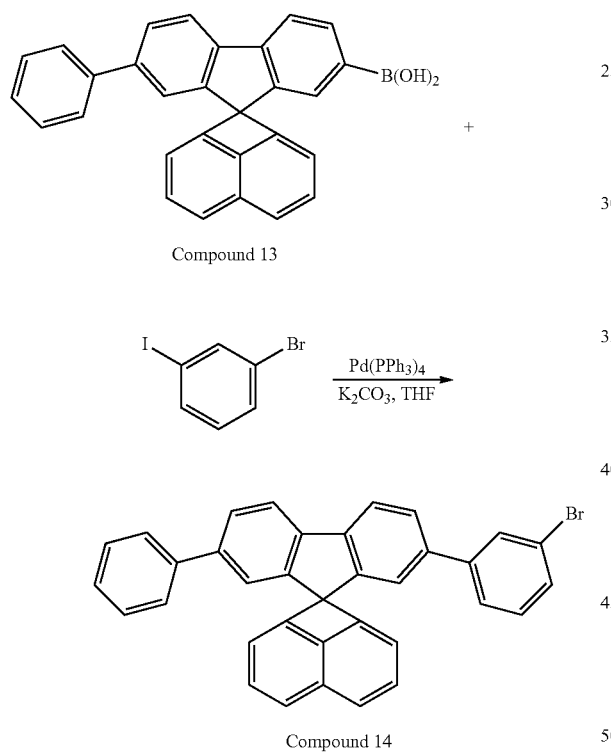

Compound 13

Compound 14

Under a nitrogen atmosphere, Compound 13 (4.10 g, 10 mmol) and 1-bromo-3-iodobenzene (2.83 g, 10 mmol) were mixed and dissolved in tetrahydrofuran (40 mL). Then Pd(PPh$_3$)$_4$ (0.58 g, 0.5 mmol) and K$_2$CO$_3$ (2 M, 15 mL, 30 mmol) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=4:1, to obtain Compound 14 (3.81 g, 73%).

$^1$H NMR (DMSO, 300 Hz): δ(ppm)=8.10-7.78 (m, 4H), 7.76-7.25 (m, 13H), 7.22-6.90 (m, 2H), 6.87-6.60 (d, 2H)

Compound 14 MS(FAB): 521(M$^+$)

Synthesis of Intermediate 7

[Reaction equation 16]

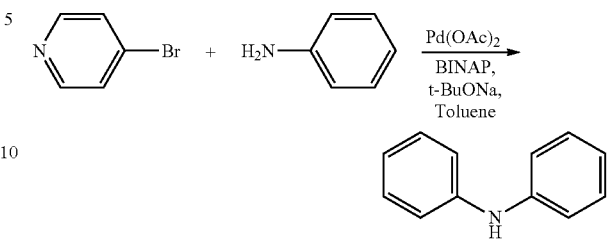

Intermediate 7

Under a nitrogen atmosphere, 2-bromopyridine (1.58 g, 10 mmol) and aniline (2.79 g, 30 mmol) were mixed and dissolved in toluene (40 mL). Then t-BuONa (2.88 g, 30 mmol), Pd(OAc)$_2$ (45 mg, 0.2 mmol), and BINAP (0.25 g, 0.4 mmol) were added and refluxed for 2 hrs.

After the reaction was terminated, the reactants were cooled to normal temperature, and MC (150 mL) and H$_2$O (150 mL) were added. The MC layer was extracted, dried over anhydrous MgSO$_4$, concentrated, and purified by column chromatography eluting with Hex:EA=4:1, to obtain Intermediate 7 (1.24 g, 73%).

Intermediate 7 MS(FAB): 170(M+)

Synthesis of Compound 15

[Reaction equation 17]

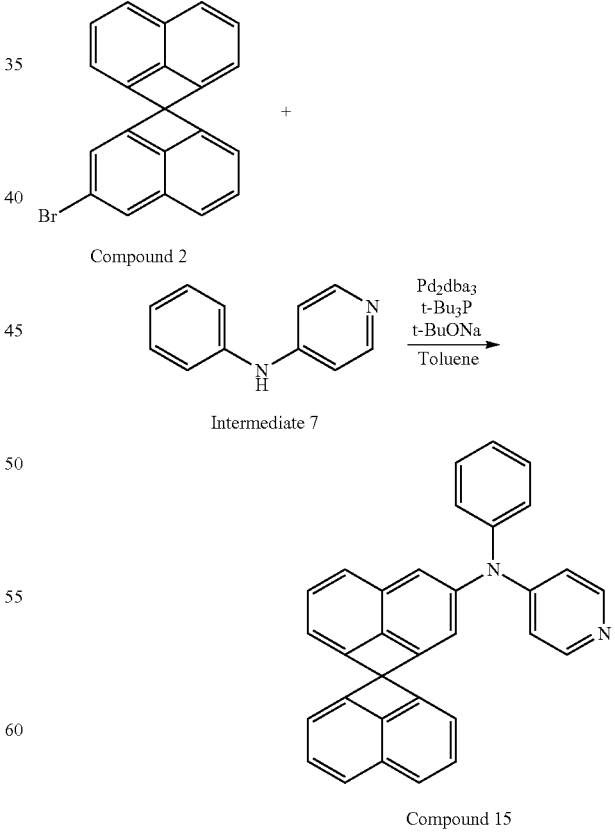

Compound 2

Intermediate 7

Compound 15

Under a nitrogen atmosphere, Compound 2 (3.43 g, 10 mmol) and Intermediate 7 (1.70 g, 10 mmol) were mixed and dissolved in toluene (50 mL). Then Pd$_2$dba$_3$ (0.18 g, 0.2 mmol), t-Bu$_3$P (0.4 ml, 0.4 mmol), and t-BuONa (2.88 g, 30 mmol) were added and refluxed for 12 hrs.

After the reaction was terminated, MC (250 mL) and H$_2$O (250 mL) were added. The MC layer was extracted, and the organic layer was distilled under reduced pressure and purified by column chromatography eluting with Hex:EA=2:1, to obtain Compound 15 (3.29 g, 76%).

1H NMR (DMSO, 300 Hz): δ(ppm)=8.55-8.25 (d, 2H), 8.21-8.10 (m, 1H), 8.10-7.80 (m, 2H), 7.75-6.90 (m, 11H), 6.90-6.55 (m, 4H).

Compound 15 MS(FAB): 432(M+).

Synthesis of Compound 16

[Reaction equation 18]

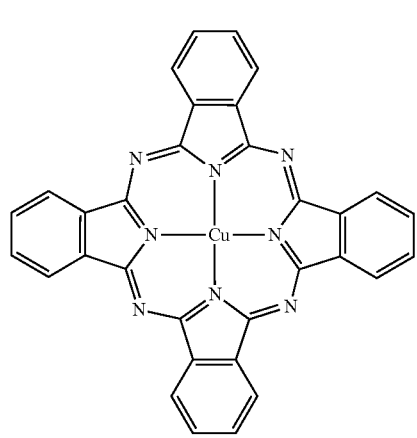

Compound 16

Under a nitrogen atmosphere, Compound 6 (3.69 g, 10 mmol) and Intermediate 7 (1.70 g, 10 mmol) were mixed and dissolved in toluene (50 mL). Then, Pd$_2$dba$_3$ (0.18 g, 0.2 mmol), t-Bu$_3$P (0.4 ml, 0.4 mmol), and t-BuONa (2.88 g, 30 mmol) were added and refluxed for 12 hrs.

After the reaction was terminated, MC (250 mL) and H$_2$O (250 mL) were added. The MC layer was extracted, and the organic layer was distilled under reduced pressure and purified by column chromatography eluting with Hex:EA=2:1, to obtain Compound 16 (3.58 g, 76%).

1H NMR (DMSO, 300 Hz): δ(ppm)=8.57-8.25 (d, 2H), 8.21-8.10 (m, 1H), 8.10-7.75 (m, 2H), 7.72-6.90 (m, 13H), 6.90-6.52 (m, 4H).

Compound 16 MS(FAB): 458(M+).

Hereinafter, the present invention is described in further detail with reference to examples. However, the examples are merely illustrative of the present invention more specifically, and the protection scope of the present invention is not limited thereto. Appropriate modifications and changes may be made to the examples by those skilled in the art without departing from the protection scope of the present invention.

Example 1

An ITO anode (5 Ω/cm$^2$, 1200 Å) coated glass substrate was cut to have a size of 45 mm×45 mm×0.7 mm, ultra-sonicated for 5 min in isopropanol and pure water, rinsed for 30 min with ozone under UV irradiation, and then disposed on a vacuum coating equipment.

On the top of the ITO coating, CuPC of about 300 Å in thickness denoted by Ex-1 below, NPD of about 900 Å in thickness denoted by Ex-2 below, DPBVi of about 200 Å denoted by Ex-3 below (which is doped with about 1% of the substance denoted by Ex-4 below), Compound 15 of the present invention as an electron transport layer of about 350 Å in thickness, LiF of about 10 Å in thickness, and aluminium (Al) of about 1000 Å in thickness were deposited in sequence.

Example 2

This example was the same as Example 1 except that Compound 16 was used as the electron transport layer in place of Compound 15.

Comparative Example 1

This example was the same as Example 1 except that Alq$_3$ denoted by Ex-5 was used as the electron transport layer in place of Compound 15.

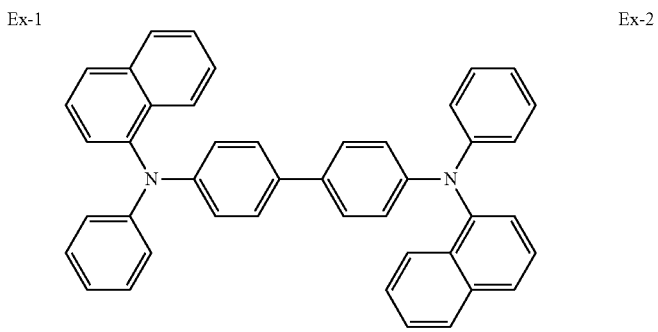

-continued

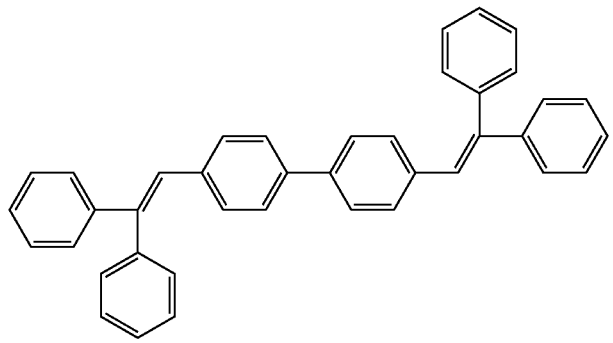
Ex-3

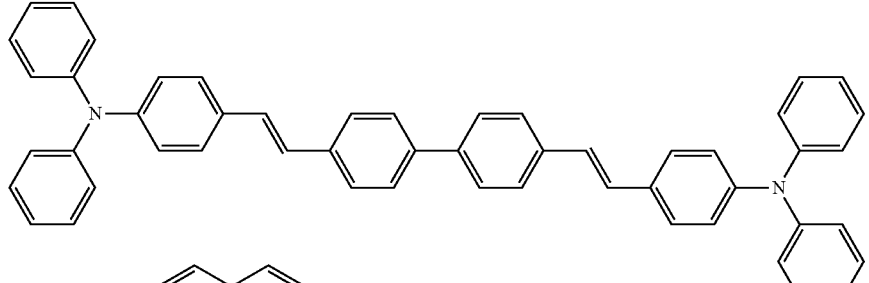
Ex-4

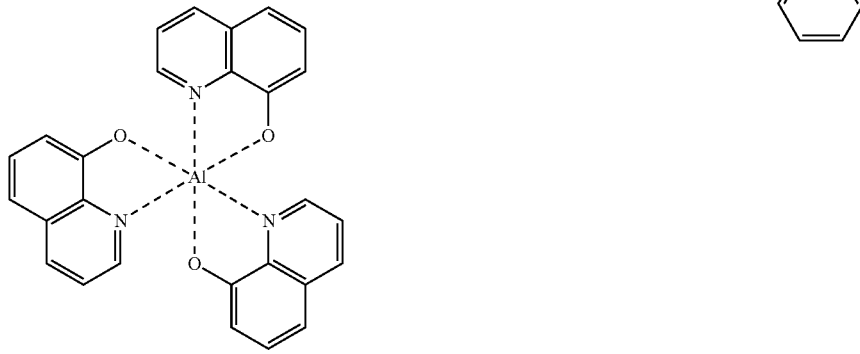
Ex-5

Experiment Example: Characteristic Evaluation of Organic Electroluminescence Devices The characteristics of the organic electroluminescence devices 1 and 2 fabricated in the examples above and the organic electroluminescence device fabricated in the comparative example were determined at a current density of 10 mA/cm². The results are shown in Table 1.

TABLE 1

| Material | Current density (mA/cm²) | Voltage (V) | Luminous efficiency (Cd/A) | CIE system (X Y) |
|---|---|---|---|---|
| Comparative Example 1 Alq₃ | 10 | 5.2 | 4.10 | (0.137 0.189) |
| Example 1 Compound 15 | 10 | 4.8 | 5.71 | (0.136 0.187) |
| Example 2 Compound 16 | 10 | 4.9 | 5.53 | (0.136 0.189) |

As shown in Table 1 above, the organic electroluminescence devices fabricated in Examples 1 and 2 of the present invention have obviously increased luminous efficiency, compared with the organic electroluminescence device fabricated in the comparative example.

It can be known from the experimental results above that when the organic compound of the present invention is used as an electron transport substance, the luminous efficiency of the organic electroluminescence devices is increased. Therefore, the organic compound of the present invention enables the device to be driven at a low voltage, and can reduce the power consumption as well. Furthermore, due to being driven with a low power, the luminous life of the organic electroluminescence devices is also enhanced.

What is claimed is:

1. An organic compound represented by General Formula (1):

[General Formula 1]

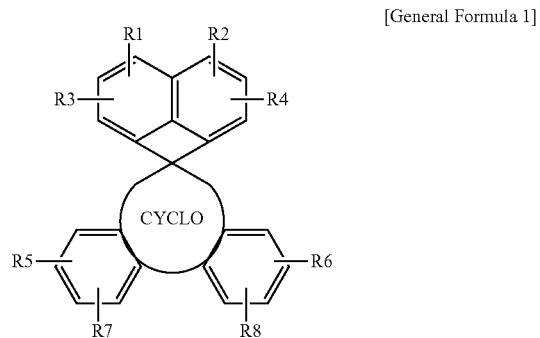

wherein
CYCLO is a ring having 4 or 5 carbon atoms, provided that when the CYCLO is a ring having 4 carbon atoms, two phenyl groups forming the CYCLO are taken together to form a naphthyl group; and R1, R2, R3, R4, R5, R6, R7, and R8 are each independently (i) hydrogen, deuterium, F, Cl, Br, I, CN, $Si(CH_3)_3$, $B(OH)_2$, (ii) a linear or branched alkyl having 1 to 40 carbon atoms, (iii) an alkoxy having 1 to 40 carbon atoms, (iv) a thioalkyl having 1 to 40 carbon atoms, (v) a cycloalkyl having 3 to 40 carbon atoms, (vi) an aromatic hydrocarbyl having 6 to 60 carbon atoms, which is unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, a cycloalkyl having 3 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl, (vii) a heteroaromatic hydrocarbyl having 5 to 60 carbon atoms and one or more elements selected from the group consisting of S, O, N, and Si, which is unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, a cycloalkyl having 3 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl, or (viii) an amino group substituted with one or more selected from the group consisting of phenyl, biphenyl, naphthyl, anthryl, anthryl substituted with phenyl, phenanthryl, pyrenyl, 9,9-dimethylfluorenyl, carbazolyl, quinolinyl, dibenzofuranyl, pyrrolyl, triazolyl, pyridinyl, pyrazinyl, pyrimidinyl, where the phenyl, biphenyl, naphthyl, anthryl, and the phenyl substituent attached to the anthryl group are unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, and a cycloalkyl having 3 to 40 carbon atoms.

2. The organic compound according to claim 1, wherein the organic compound is represented by General Formula (2) or (3) below:

[General Formula 2]

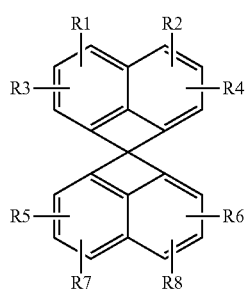

[General Formula 3]

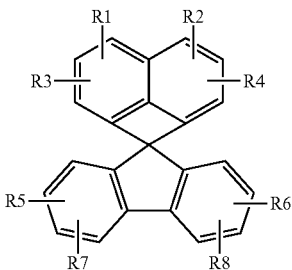

wherein in the formulas
R1, R2, R3, R4, R5, R6, R7, and R8 are each independently (i) hydrogen, deuterium, F, Cl, Br, I, CN, $Si(CH_3)_3$, $B(OH)_2$, (ii) a linear or branched alkyl having 1 to 40 carbon atoms, (iii) an alkoxy having 1 to 40 carbon atoms, (iv) a thioalkyl having 1 to 40 carbon atoms, (v) a cycloalkyl having 3 to 40 carbon atoms, (vi) an aromatic hydrocarbyl having 6 to 60 carbon atoms, which is unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, a cycloalkyl having 3 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl, (vii) a heteroaromatic hydrocarbyl having 5 to 60 carbon atoms and one or more elements selected from the group consisting of S, O, N, and Si, which is unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, a cycloalkyl having 3 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl, or (viii) an amino group substituted with one or more selected from the group consisting of phenyl, biphenyl, naphthyl, anthryl, anthryl substituted with phenyl, phenanthryl, pyrenyl, 9,9-dimethylfluorenyl, carbazolyl, quinolinyl, dibenzofuranyl, pyrrolyl, triazolyl, pyridinyl, pyrazinyl, and pyrimidinyl, where the phenyl, biphenyl, naphthyl, anthryl, and the phenyl substituent attached to the anthryl group are unsubstituted or substituted with one or more selected from the group consisting of F, Cl, Br, I, CN, $Si(CH_3)_3$, $B(OH)_2$, a linear or branched alkyl having 1 to 40 carbon atoms, an alkoxy having 1 to 40 carbon atoms, a thioalkyl having 1 to 40 carbon atoms, and a cycloalkyl having 3 to 40 carbon atoms.

3. The organic compound according to claim 2, wherein:
R1, R2, R3, R4, R5, R6, R7, and R8 are each independently (i) hydrogen, deuterium, F, Cl, Br, I, CN, $Si(CH_3)_3$, $B(OH)_2$, (ii) a linear or branched alkyl having 1 to 40 carbon atoms, (iii) phenyl, biphenyl, naphthyl, anthryl, phenanthryl, or pyrenyl unsubstituted or substituted with one or more selected from the group consisting of F, Cl, Br, I, B(OH)$_2$, a linear or branched alkyl having 1 to 40 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, pyrimidinyl, and quinolinyl, (iv) pyrrolyl, triazolyl, pyridinyl, pyrazinyl, pyrimidinyl, quinolinyl, 9,9-dimethylfluorenyl, carbazolyl or dibenzofuranyl unsubstituted or substituted with one or more selected from the group consisting of F, Cl, Br, I, B(OH)$_2$, a linear or branched alkyl having 1 to 10 carbon atoms, phenyl, biphenyl, naphthyl, anthryl, anthryl substituted with phenyl, phenanthryl, pyrenyl, 9,9-dimethylfluorenyl, carbazolyl, dibenzofuranyl, pyrrolyl, triazolyl, pyridinyl, pyrazinyl, and pyrimidinyl, or (v) an amino group substituted with one or more selected from the group consisting of F, Cl, Br, I, B(OH)$_2$, a linear or branched alkyl having 1 to 10 carbon atoms, phenyl, biphenyl, naphthyl, anthryl, anthryl substituted with phenyl, phenanthryl, pyrenyl, 9,9-dimethylfluorenyl, carbazolyl, quinolinyl, and dibenzofuranyl.

4. The organic compound according to claim 2, wherein the organic compound is any one of the compounds below:

1
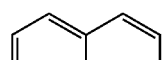

2
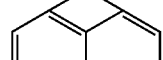

3
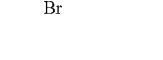

-continued

4
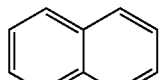

5
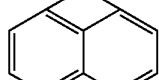

6
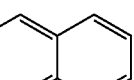

7
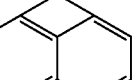

8
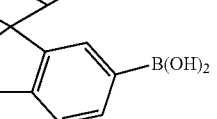

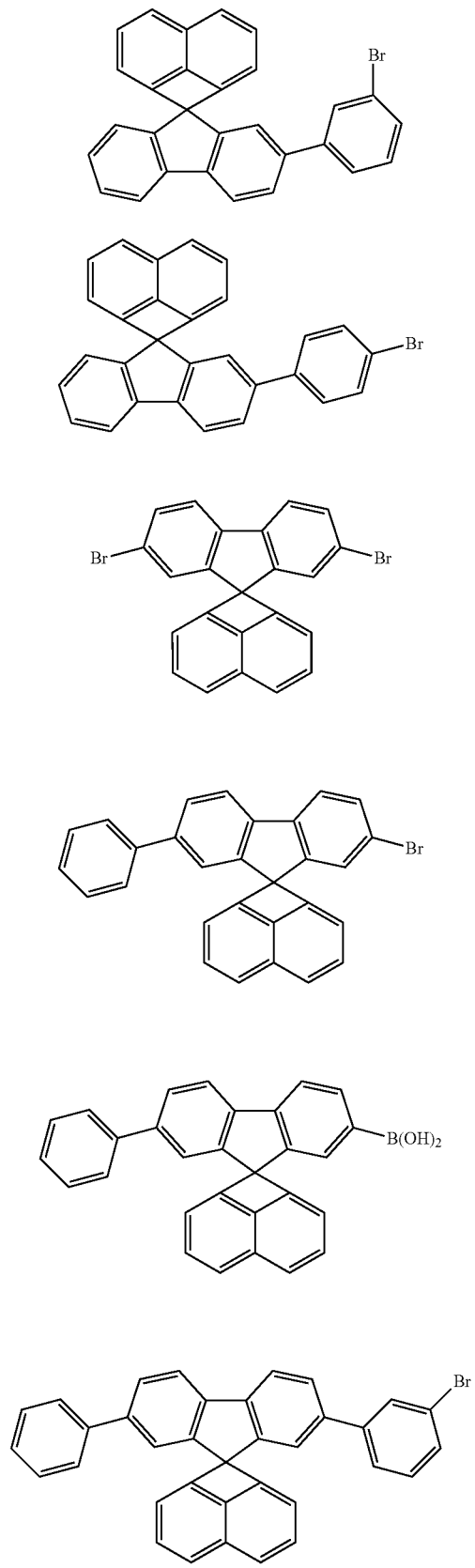
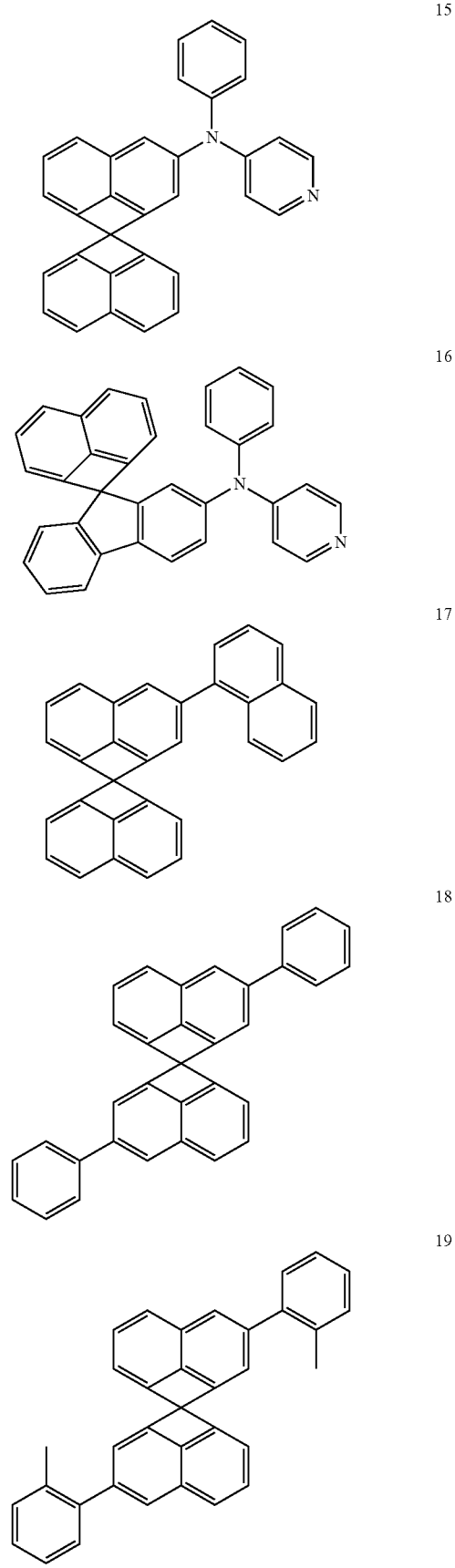

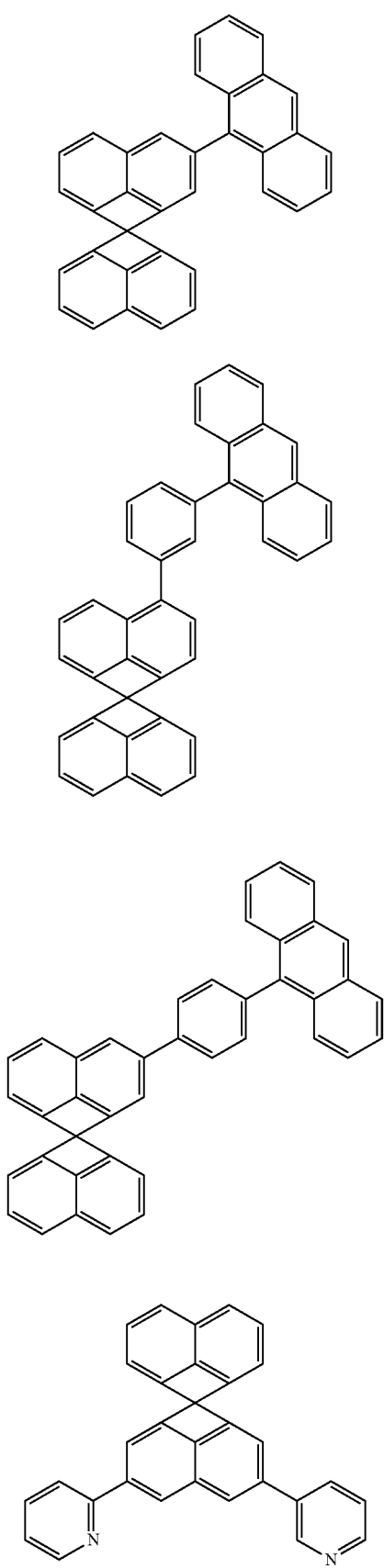
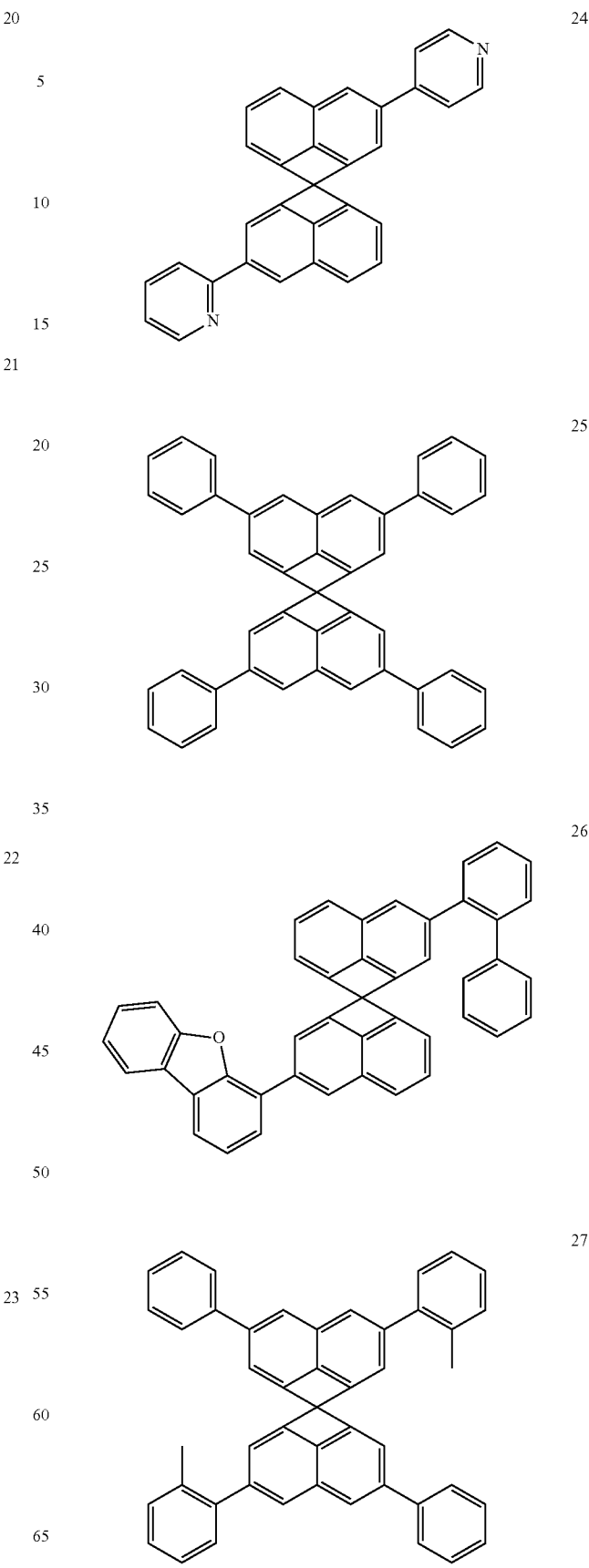

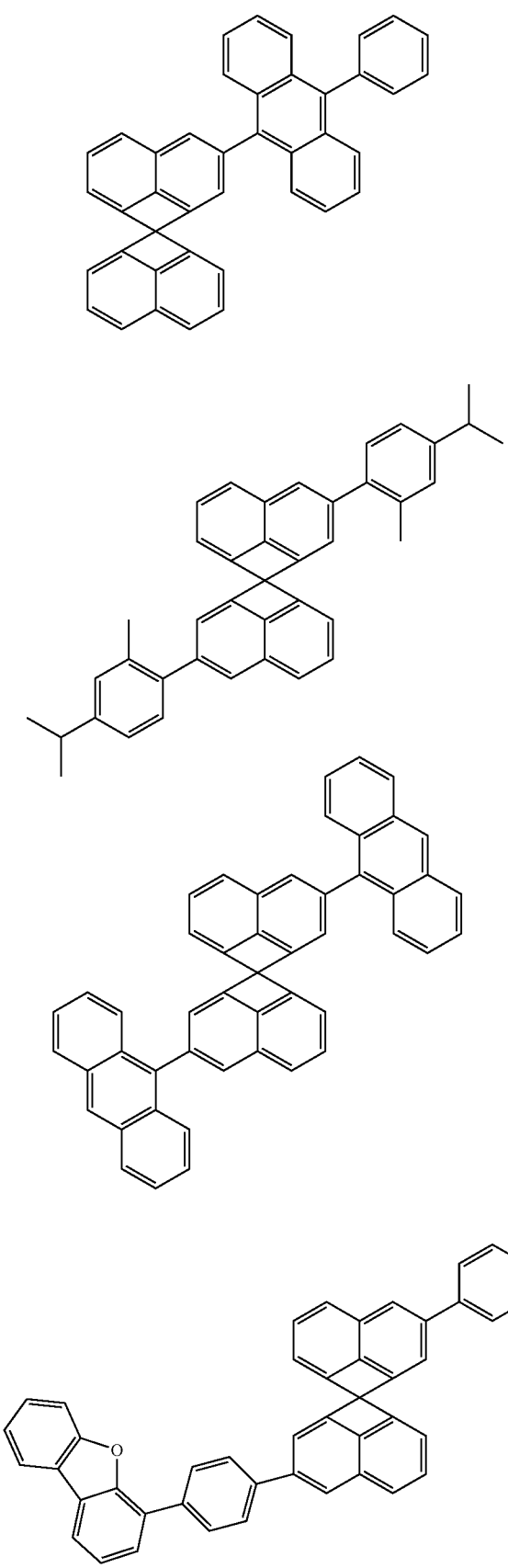
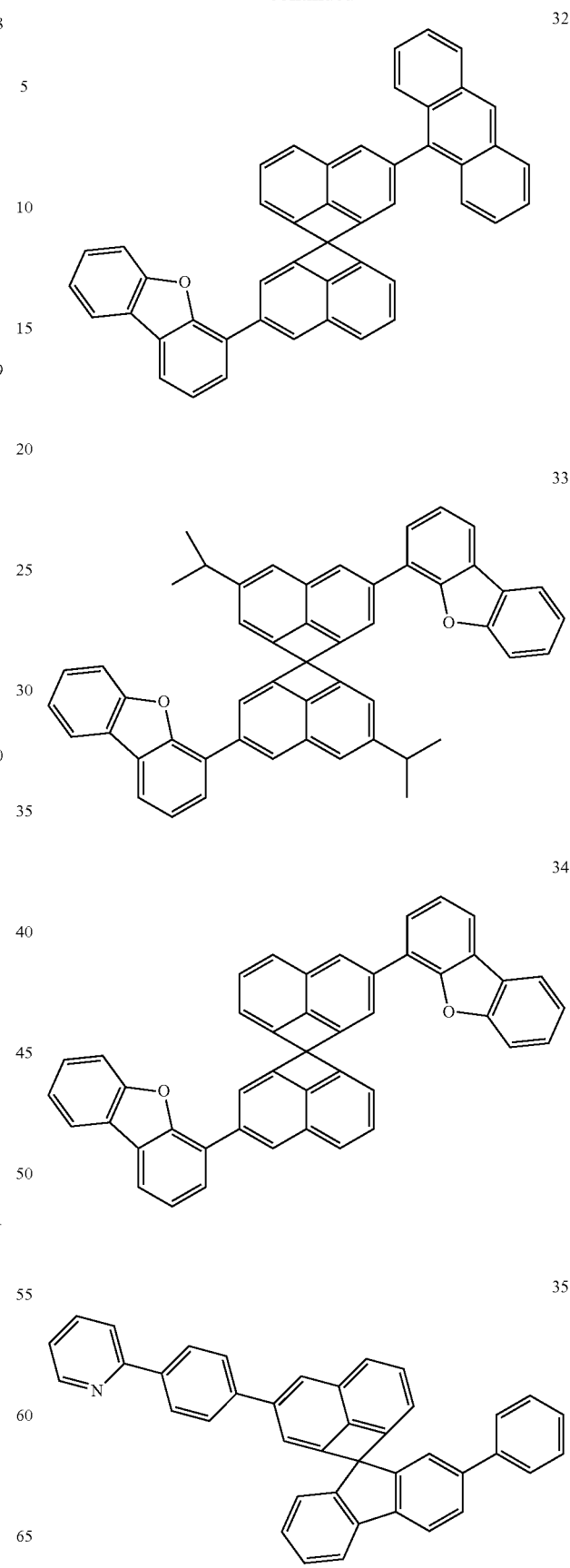

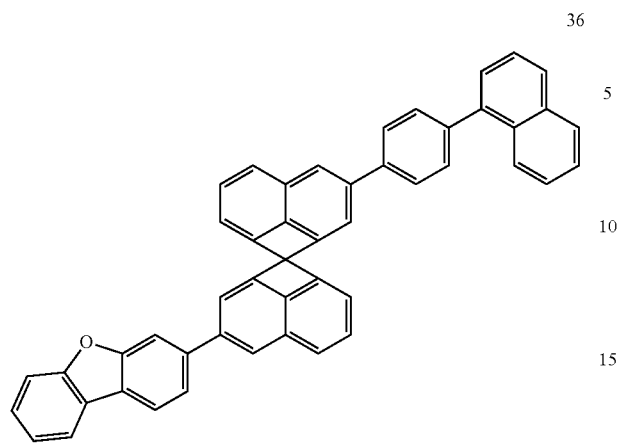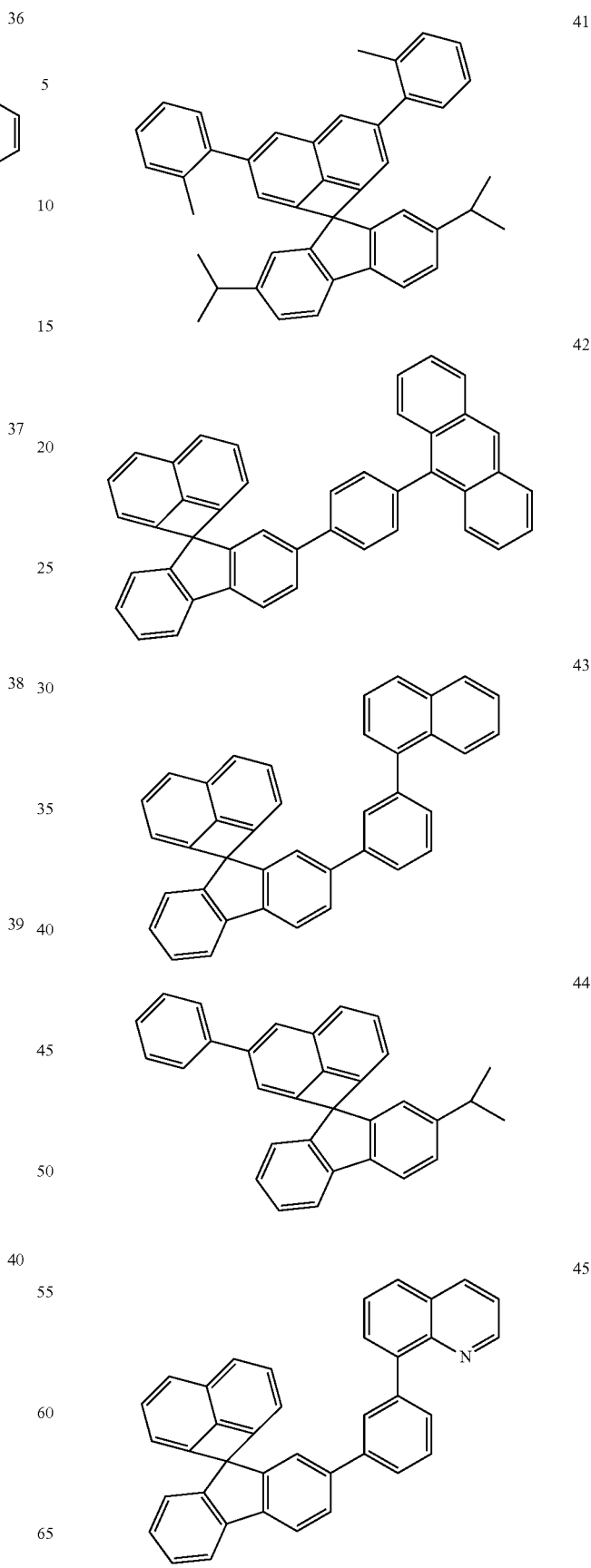

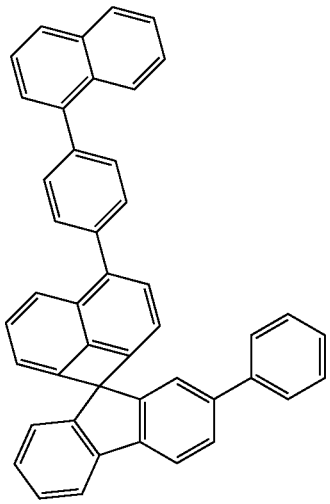

46

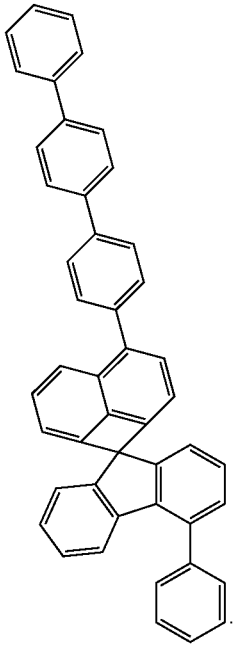

48

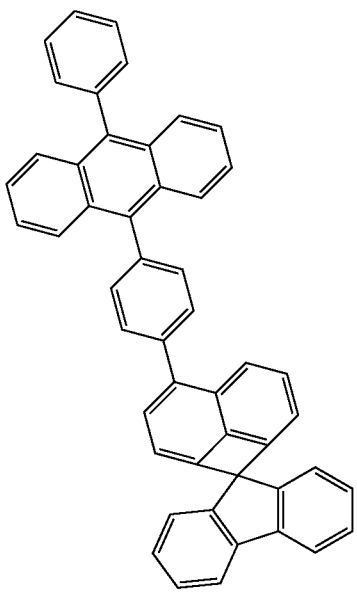

47

5. A material for forming a hole injection layer substance, a hole transport layer substance, an electron blocking layer substance, an emission layer substance, a hole blocking layer substance, an electron transport layer substance or an electron injection layer material for an organic electroluminescence device, the material comprising the organic compound according to claim 1.

6. An organic electroluminescence device, having one or more organic thin film layers, including at least an emission layer, sandwiched between a cathode and an anode, wherein at least one of the organic thin film layers contains one or two or more of the organic compound according to claim 1.

7. The organic electroluminescence device according to claim 6, wherein the organic electroluminescence device has a structure comprising the anode, a hole injection layer, a hole transport layer, an electron blocking layer, the emission layer, a hole blocking layer, an electron transport layer, an electron injection layer, and the cathode laminated in sequence.

* * * * *